(12) United States Patent
Ulreich et al.

(10) Patent No.: US 11,890,221 B2
(45) Date of Patent: Feb. 6, 2024

(54) DEVICES AND SYSTEMS FOR URINE COLLECTION

(71) Applicant: Sage Products LLC, Cary, IL (US)

(72) Inventors: Daniel R. Ulreich, Cary, IL (US); Brett C. Blabas, Naperville, IL (US); Kristin M. Sexton, Cary, IL (US); Catherine S. Boulos, Vernon Hills, IL (US); Britt O'Halloran, Crystal Lake, IL (US)

(73) Assignee: Sage Products, LLC, Cary, IL (US)

( * ) Notice: Subject to any disclaimer, the term of this patent is extended or adjusted under 35 U.S.C. 154(b) by 667 days.

(21) Appl. No.: 17/013,822

(22) Filed: Sep. 7, 2020

(65) Prior Publication Data

US 2021/0069008 A1 Mar. 11, 2021

Related U.S. Application Data

(60) Provisional application No. 62/897,058, filed on Sep. 6, 2019.

(51) Int. Cl.
| | |
|---|---|
| *A61F 5/455* | (2006.01) |
| *A61F 5/441* | (2006.01) |
| *A61F 5/443* | (2006.01) |

(52) U.S. Cl.
CPC .............. *A61F 5/455* (2013.01); *A61F 5/441* (2013.01); *A61F 5/443* (2013.01)

(58) Field of Classification Search
CPC ........... A61F 5/455; A61F 5/441; A61F 5/443
See application file for complete search history.

(56) References Cited

U.S. PATENT DOCUMENTS

| | | |
|---|---|---|
| 3,349,768 A | 10/1967 | Keane |
| 3,528,423 A | 9/1970 | Lee et al. |
| | (Continued) | |

FOREIGN PATENT DOCUMENTS

| | | |
|---|---|---|
| EP | 1 616 542 B1 | 1/2006 |
| GB | 2199750 | 7/1988 |
| | (Continued) | |

OTHER PUBLICATIONS

English translation of Abstract of Japanese Patent Application No. 2001-276107 dated Jun. 1, 2021.

(Continued)

*Primary Examiner* — Guy K Townsend
(74) *Attorney, Agent, or Firm* — McDonnell Boehnen Hulbert & Berghoff LLP

(57) ABSTRACT

In an example, a urine collection device includes a covering defining a recessed receptacle and a fluid collection assembly positioned in the recessed receptacle. The fluid collection assembly includes (i) a foam sleeve including a bore, (ii) a shape retaining element positioned in the bore of the foam sleeve and defining a passage, and (iii) a tube extending through the passage defined by the shape retaining element. The shape retaining element can conform the fluid collection assembly to a curved configuration and maintain the curved configuration of the fluid collection assembly until the curved configuration is adjusted. The urine collection further includes a top sheet coupled to the covering. The top sheet and the covering define an internal chamber of the urine collection device. The top sheet is configured to draw urine into the internal chamber and toward the fluid collection assembly.

20 Claims, 19 Drawing Sheets

(56) References Cited

U.S. PATENT DOCUMENTS

| | | | |
|---|---|---|---|
| 3,613,123 A | 10/1971 | Langstrom | |
| 3,661,155 A * | 5/1972 | Lindan | A61F 5/455 128/835 |
| 3,722,503 A * | 3/1973 | Hovick | A61F 5/44 4/144.3 |
| 4,681,572 A * | 7/1987 | Tokarz | A61B 1/307 600/587 |
| 4,747,166 A | 5/1988 | Kuntz | |
| 4,804,377 A | 2/1989 | Hanifl et al. | |
| 4,820,297 A | 4/1989 | Kaufman et al. | |
| 4,846,818 A * | 7/1989 | Keldahl | A61F 5/455 600/574 |
| 4,886,508 A | 12/1989 | Washington | |
| 5,049,144 A * | 9/1991 | Payton | A61F 5/455 600/574 |
| 5,678,564 A * | 10/1997 | Lawrence | A61F 5/455 600/573 |
| 6,551,292 B1 | 4/2003 | D'Acchioli et al. | |
| 6,569,133 B2 | 5/2003 | Cheng et al. | |
| 6,592,560 B2 | 7/2003 | Snyder | |
| 7,135,012 B2 | 11/2006 | Harvie | |
| 7,186,245 B1 | 3/2007 | Cheng et al. | |
| 7,220,250 B2 | 5/2007 | Suzuki et al. | |
| 7,390,320 B2 | 6/2008 | Machida et al. | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,727,206 B2 | 6/2010 | Gorres | |
| 7,740,620 B2 | 6/2010 | Gilbert et al. | |
| 7,749,205 B2 | 7/2010 | Tazoe et al. | |
| 7,755,497 B2 | 7/2010 | Wada et al. | |
| 7,833,169 B2 | 11/2010 | Hannon | |
| 7,939,706 B2 | 5/2011 | Okabe et al. | |
| 8,287,508 B1 | 10/2012 | Sanchez | |
| 8,303,554 B2 | 11/2012 | Tsai et al. | |
| 8,343,122 B2 | 1/2013 | Gorres | |
| 8,388,588 B2 | 3/2013 | Wada et al. | |
| 9,173,602 B2 | 11/2015 | Gilbert | |
| 9,173,799 B2 | 11/2015 | Tanimoto et al. | |
| 10,226,376 B2 | 3/2019 | Sanchez | |
| 10,376,406 B2 * | 8/2019 | Newton | A61F 5/4404 |
| 10,376,407 B2 | 8/2019 | Newton | |
| 10,390,989 B2 | 8/2019 | Sanchez | |
| D882,768 S * | 4/2020 | Blabas | A61F 5/455 D24/122 |
| 10,857,025 B2 * | 12/2020 | Davis | A61B 5/208 |
| 10,973,678 B2 | 4/2021 | Newton | |
| 11,426,303 B2 * | 8/2022 | Davis | A61F 5/4408 |
| 2001/0037098 A1 | 11/2001 | Snyder | |
| 2003/0046753 A1 | 3/2003 | Buttigieg | |
| 2004/0176731 A1 * | 9/2004 | Cheng | A61F 5/455 604/329 |
| 2004/0191919 A1 * | 9/2004 | Unger | A61J 1/1462 436/164 |
| 2004/0254547 A1 | 12/2004 | Okabe et al. | |
| 2005/0070861 A1 | 3/2005 | Okabe et al. | |
| 2005/0119630 A1 * | 6/2005 | Harvie | A61F 5/451 604/355 |
| 2006/0163097 A1 * | 7/2006 | Murray | B65D 81/22 206/364 |
| 2007/0038194 A1 | 2/2007 | Wada et al. | |
| 2007/0093840 A1 | 4/2007 | Pacelli | |
| 2008/0287894 A1 * | 11/2008 | Van Den Heuvel | A61F 5/455 604/327 |
| 2010/0241104 A1 | 9/2010 | Gilbert | |
| 2010/0286791 A1 * | 11/2010 | Goldsmith | A61B 17/12022 604/524 |
| 2011/0028922 A1 | 2/2011 | Kay et al. | |
| 2011/0077495 A1 | 3/2011 | Gilbert | |
| 2011/0172625 A1 | 7/2011 | Wada et al. | |
| 2012/0103347 A1 | 5/2012 | Wheaton et al. | |
| 2012/0116336 A1 * | 5/2012 | Sharma | A61M 25/04 604/328 |
| 2014/0157499 A1 | 6/2014 | Suzuki et al. | |
| 2016/0029998 A1 | 2/2016 | Brister et al. | |
| 2016/0258322 A1 | 3/2016 | Brister et al. | |
| 2016/0278662 A1 | 9/2016 | Brister et al. | |
| 2016/0367226 A1 | 12/2016 | Newton et al. | |
| 2016/0374848 A1 | 12/2016 | Sanchez et al. | |
| 2017/0266031 A1 | 9/2017 | Sanchez et al. | |
| 2018/0228642 A1 * | 8/2018 | Davis | A61F 5/455 |
| 2019/0282391 A1 | 9/2019 | Johannes | |
| 2019/0336319 A1 * | 11/2019 | Fallis | A61F 5/4408 |
| 2019/0365561 A1 | 12/2019 | Newton | |
| 2021/0059853 A1 * | 3/2021 | Davis | A61F 5/4408 |
| 2021/0069008 A1 * | 3/2021 | Blabas | A61F 5/451 |
| 2022/0354685 A1 * | 11/2022 | Davis | A61F 5/4408 |

FOREIGN PATENT DOCUMENTS

| | | |
|---|---|---|
| GB | 2199750 A | 7/1988 |
| JP | 2001-276107 | 10/2001 |
| WO | 01/54633 A1 | 8/2001 |

OTHER PUBLICATIONS

International Search Report and Written Opinion issued by the European Patent Office in International Application No. PCT/US2020/049628 dated Nov. 27, 2020 (14 pages).

International Search Report and Written Opinion for International Application No. PCT/US2018/018112, dated Jun. 6, 2018, 10 pages.

* cited by examiner

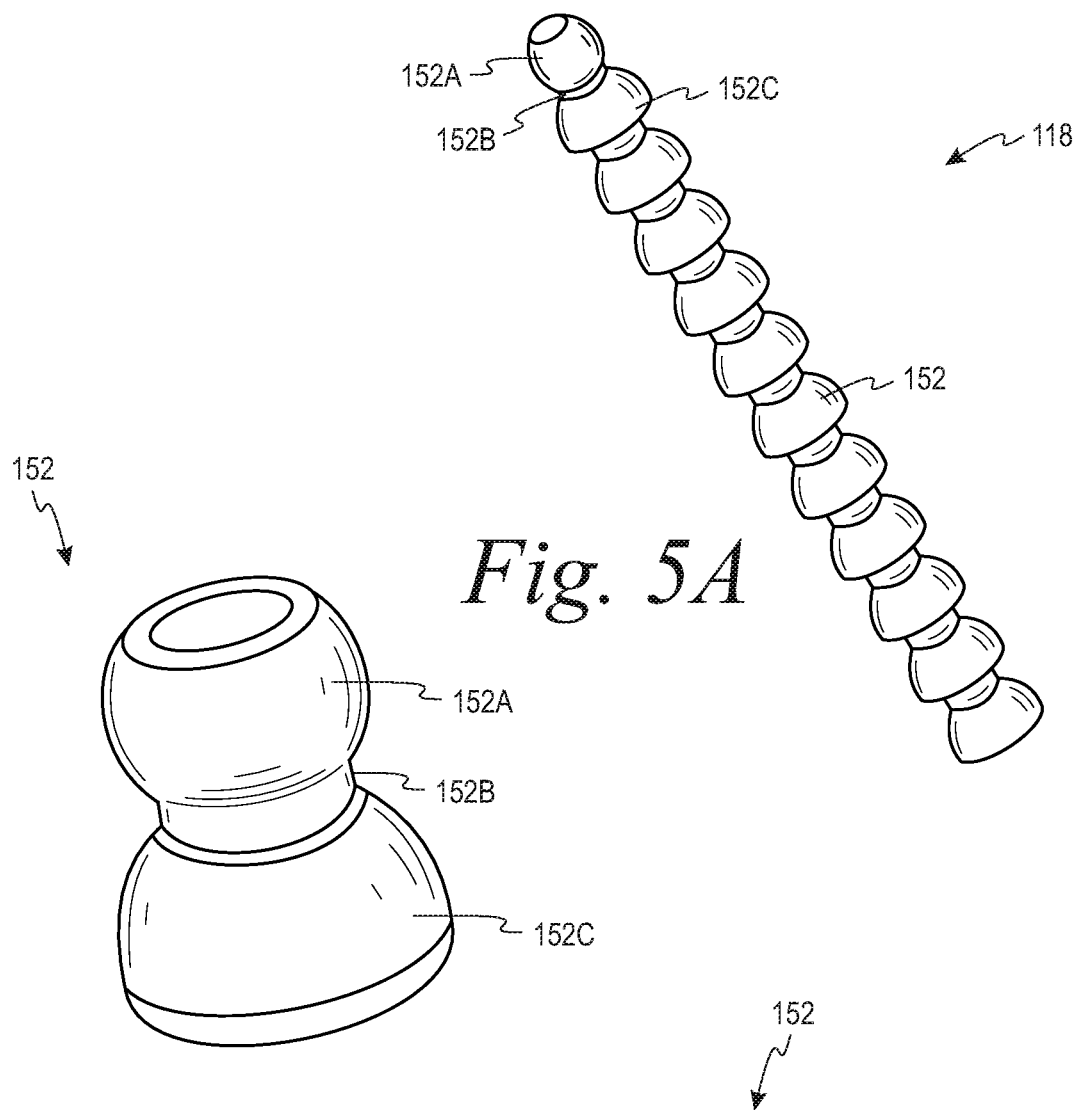
Fig. 5A
Fig. 5B
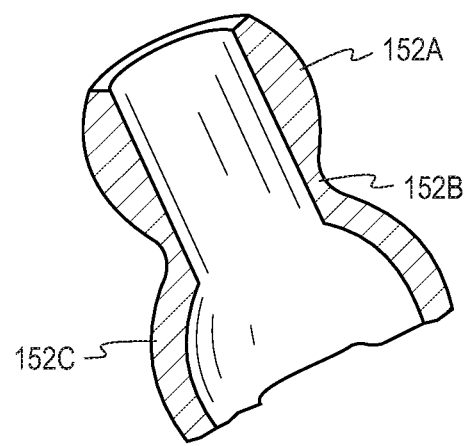
Fig. 5C

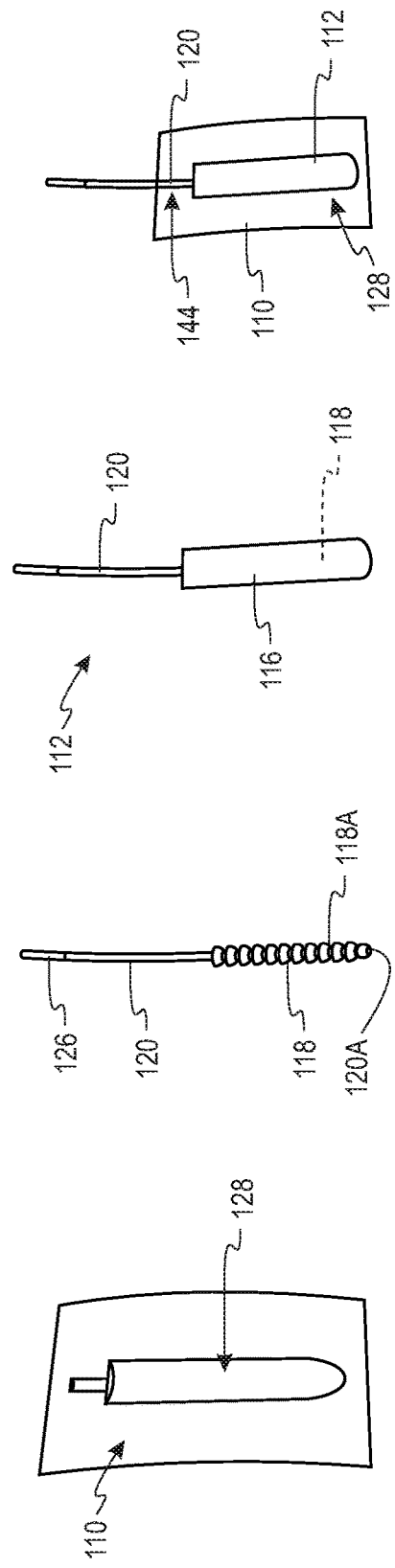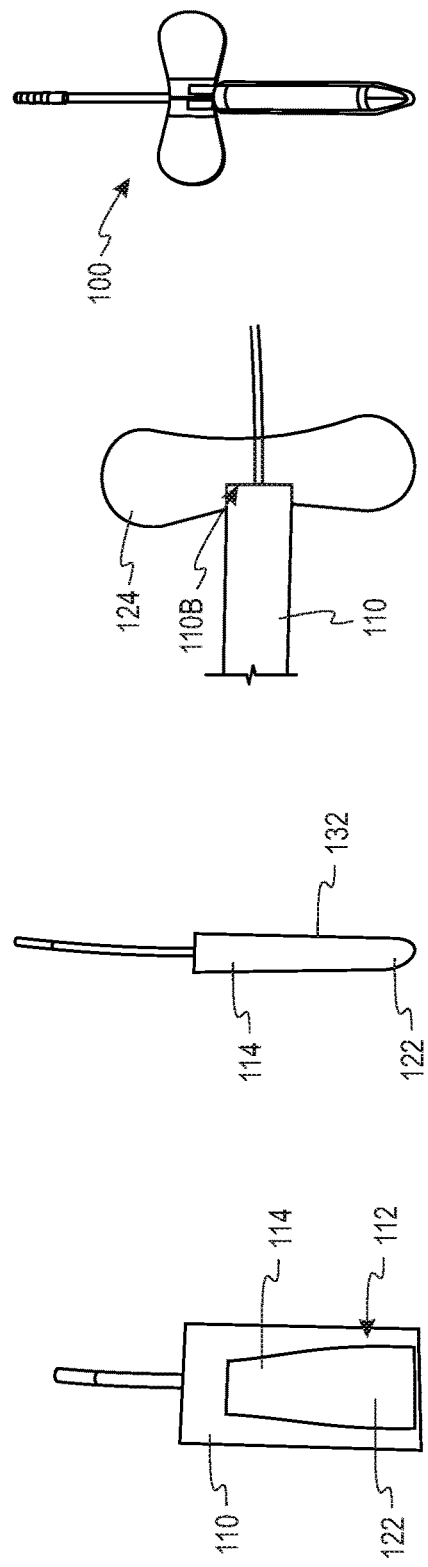

DEVICES AND SYSTEMS FOR URINE COLLECTION

CROSS-REFERENCE TO RELATED APPLICATION

The present application claims the benefit of priority to U.S. Provisional Patent Application No. 62/897,058, filed Sep. 6, 2019, the contents of which is hereby incorporated by reference in its entirety.

FIELD

The present disclosure generally relates to devices and systems for collecting urine discharged from the body of a user and carrying the urine away from the body.

BACKGROUND

Under various circumstances, a user may have limited or impaired mobility such that ordinary urinary functions and processes are rendered difficult (or impossible). For example, a person may have impaired mobility due to a disability or may be bedridden due to an injury or illness. In another example, a person may be subject to restricted occupational conditions under which the person has limited mobility. Also, for example, urine collection may be needed for monitoring purposes, such as for monitoring inputs and outputs in a clinical setting (e.g., in an intensive care unit, or for other clinical and/or laboratory testing).

Various approaches have been developed to address some of the problems or circumstances related to impaired or restricted urinary processes. However, prior approaches suffer from problems or limitations of their own. Internal urinary catheters, for example, can address problems arising from urinary incontinence or limited mobility, but urinary catheters can often be uncomfortable and can contribute to complications (for example, infections). Bed pans, as another example, are containers occasionally used for collecting urinary output of a bedridden person (such as a patient at a health care facility), but bed pans can contribute to patient discomfort, spillage, and issues related to sanitation or hygiene.

Other more recent approaches to urinary collection have been developed, which include a urine collection device configured to be placed external to, but in contact with the body for collecting and directing a fluid receptacle. However, the recent approaches also present challenges, such as in maintaining the placement of the device in appropriate contact with the body of a user, resulting in potential leakage and patient discomfort.

SUMMARY

In an example, a urine collection device is described. The urine collection device includes a covering defining a recessed receptacle, and a fluid collection assembly positioned in the recessed receptacle defined by the covering. The fluid collection assembly includes (i) a foam sleeve including a bore extending from a first end of the foam sleeve to a second end of the foam sleeve and (ii) a shape retaining element positioned in the bore of the foam sleeve. The shape retaining element is configured to conform the fluid collection assembly to a curved configuration for placement against a body of a user and maintain the curved configuration of the fluid collection assembly until the curved configuration is adjusted. The shape retaining element defines a passage extending from between a proximal end of the shape retaining element and a distal end of the shape retaining element. The fluid collection assembly also includes (iii) a tube extending through the passage defined by the shape retaining element.

The urine collection further includes a top sheet coupled to the covering. The top sheet and the covering define an internal chamber of the urine collection device. The top sheet is configured to draw urine into the internal chamber and toward the fluid collection assembly.

In another example, a method of making a urine collection device is described. The method includes forming a covering such that the covering defines a recessed receptacle and forming a fluid collection assembly. The fluid collection assembly includes (i) a foam sleeve including a bore extending from a first end of the foam sleeve to a second end of the foam sleeve and (ii) a shape retaining element positioned in the bore of the foam sleeve. The shape retaining element is configured to conform the fluid collection assembly to a curved configuration for placement against a body of a user and maintain the curved configuration of the fluid collection assembly until the curved configuration is adjusted. The shape retaining element defines a passage extending from between a proximal end of the shape retaining element and a distal end of the shape retaining element. The fluid collection assembly also includes (iii) a tube extending through the passage defined by the shape retaining element.

The method also includes positioning the fluid collection assembly in the recessed receptacle defined by the covering, wherein the fluid collection assembly; and coupling a top sheet to the covering with the fluid collection assembly positioned between the top sheet and the covering. The top sheet and the covering define an internal chamber of the urine collection device. The top sheet is configured to draw urine into the internal chamber and toward the fluid collection assembly.

In another example, a method of collecting urine discharged from a body of a user is described. The method includes providing a urine collection device. The urine collection device includes a covering defining a recessed receptacle, and a fluid collection assembly positioned in the recessed receptacle defined by the covering. The fluid collection assembly includes (i) a foam sleeve including a bore extending from a first end of the foam sleeve to a second end of the foam sleeve and (ii) a shape retaining element positioned in the bore of the foam sleeve. The shape retaining element is configured to conform the fluid collection assembly to a curved configuration for placement against a body of a user and maintain the curved configuration of the fluid collection assembly until the curved configuration is adjusted. The shape retaining element defines a passage extending from between a proximal end of the shape retaining element and a distal end of the shape retaining element. The fluid collection assembly also includes (iii) a tube extending through the passage defined by the shape retaining element. The urine collection further includes a top sheet coupled to the covering. The top sheet and the covering define an internal chamber of the urine collection device. The top sheet is configured to draw urine into the internal chamber and toward the fluid collection assembly.

Additionally, the method includes positioning the urine collection device against the body of the user with the top sheet in operative relation with a urethral opening of the user. The method also includes receiving, through the top sheet and by the fluid collection assembly, urine discharged from the urethral opening. The method further includes evacuating the urine from the fluid collection assembly through the tube.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

FIG. 5A depicts a shape retaining element of the urine collection device, according to an example.

FIG. 5B depicts a linking segment of the shape retaining element shown in FIG. 5A.

FIG. 5C depicts a cross-sectional view of the linking segment shown in FIG. 5B.

FIG. 7A depicts a stage of a process for making a urine collection device, according to an example.

FIG. 7B depicts another stage of a process for making a urine collection device, according to an example.

FIG. 7C depicts another stage of a process for making a urine collection device, according to an example.

FIG. 7D depicts another stage of a process for making a urine collection device, according to an example.

FIG. 7E depicts another stage of a process for making a urine collection device, according to an example.

FIG. 7F depicts another stage of a process for making a urine collection device, according to an example.

FIG. 7G depicts another stage of a process for making a urine collection device, according to an example.

FIG. 7H depicts another stage of a process for making a urine collection device, according to an example.

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Referring now to FIGS. 1A-1D a urine collection device 100 is shown according to an example. In particular, FIG.

Figure 1A:
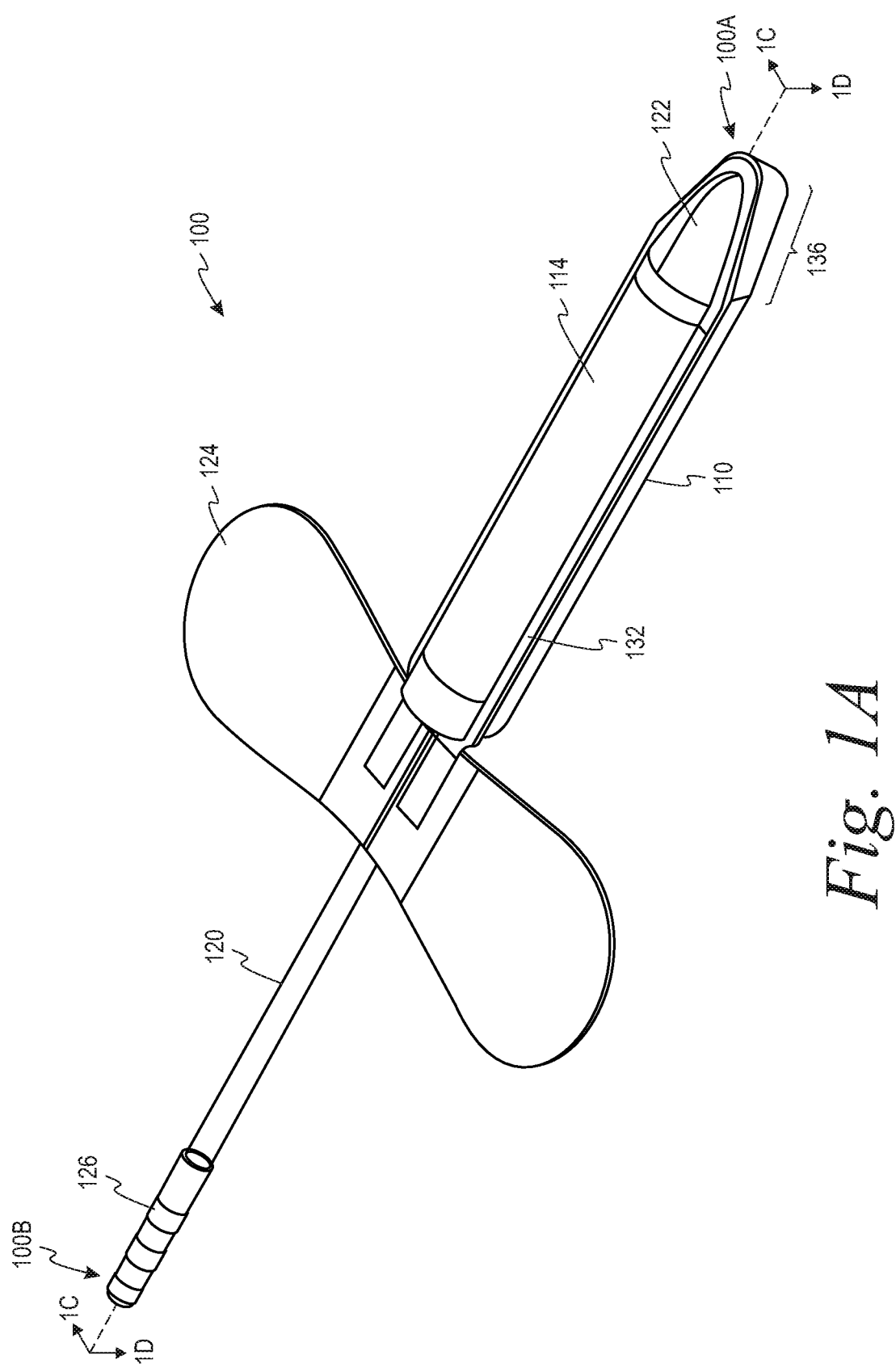
FIG. 1A depicts a perspective view of a urine collection device, according to an example.
Figure 1B:
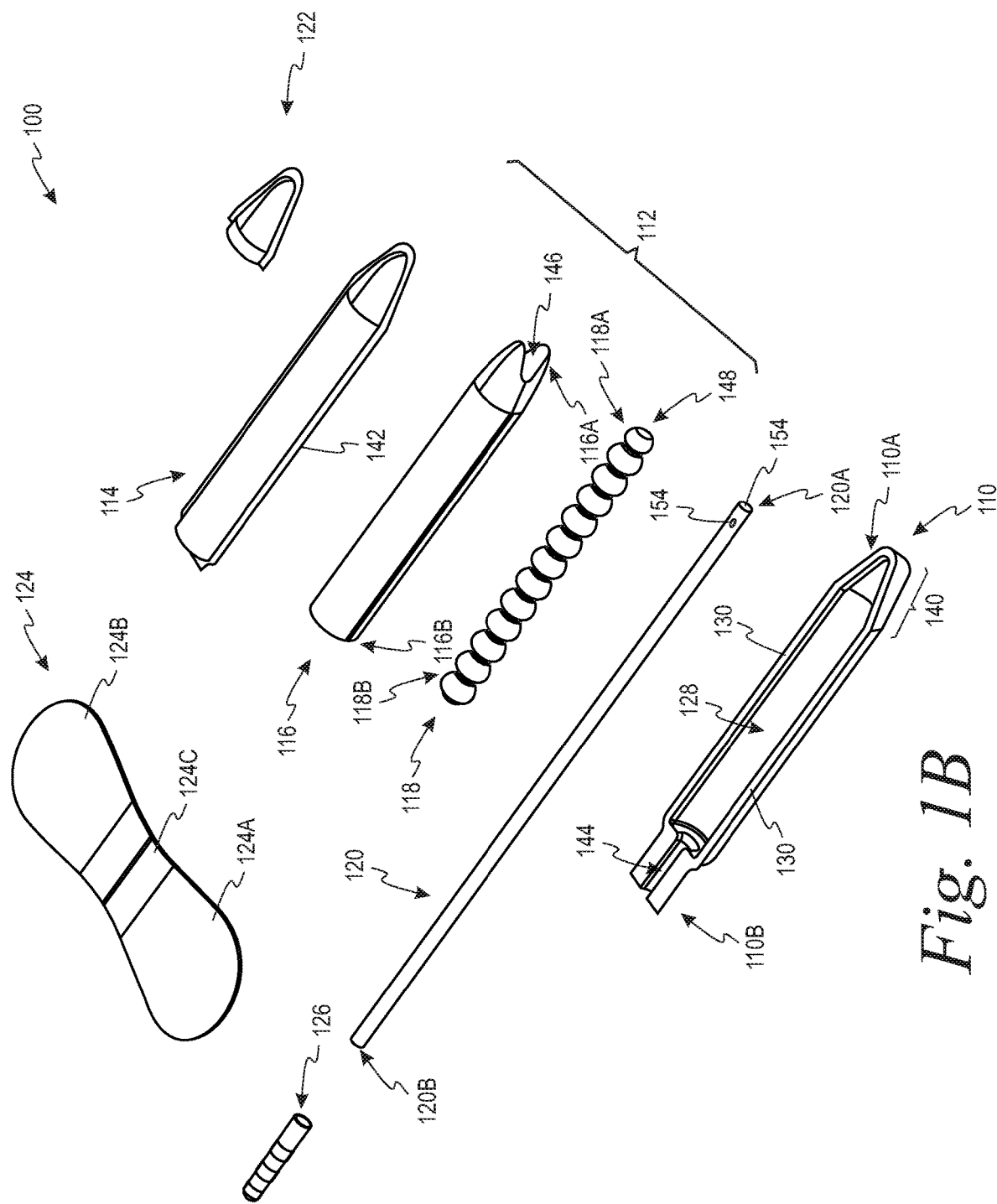
FIG. 1B depicts an exploded view of the urine collection device shown in FIG. 1A.
Figure 1C:
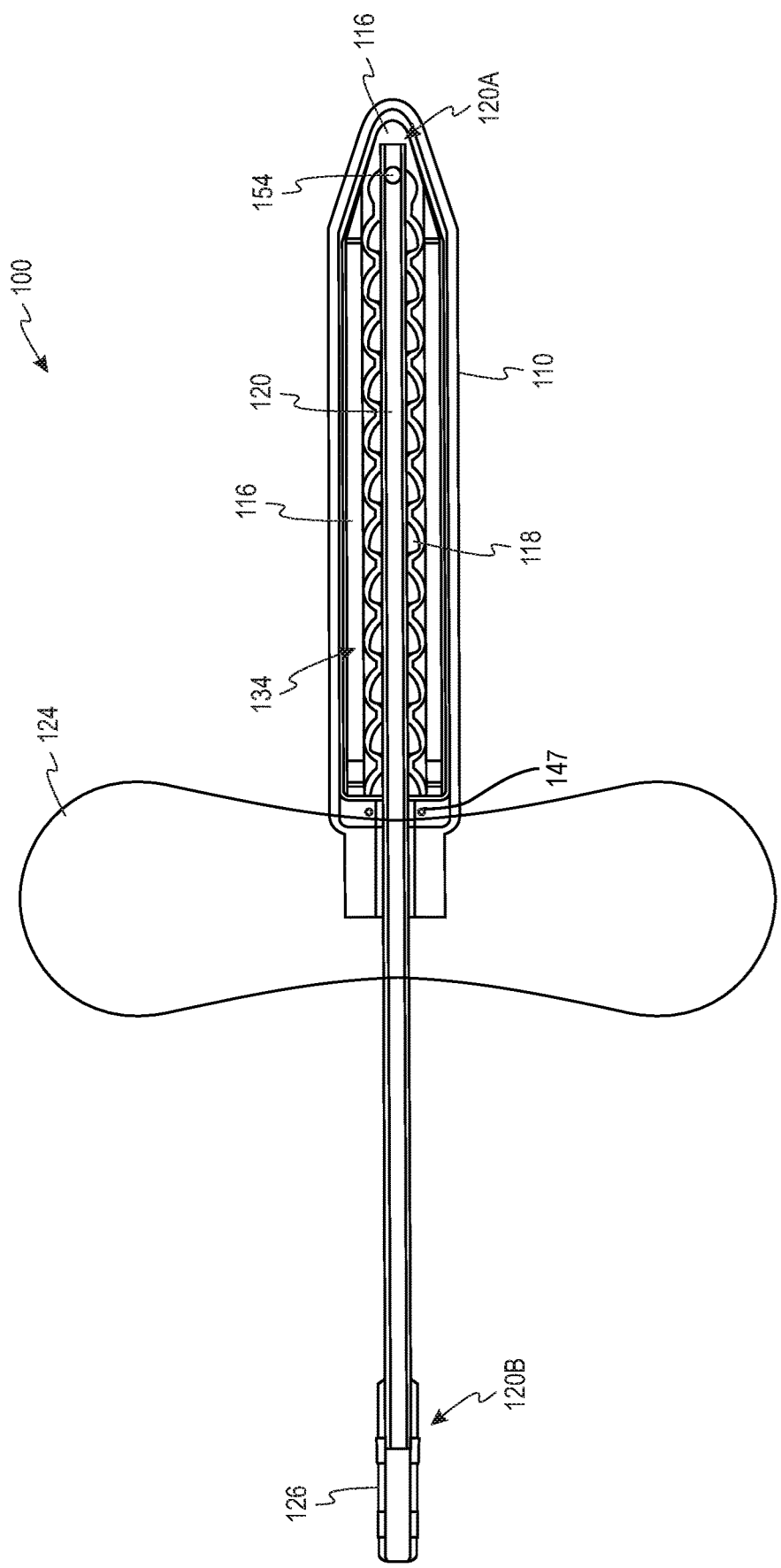
FIG. 1C depicts a cross-sectional view of the urine collection device shown in FIG. 1A.
Figure 1D:
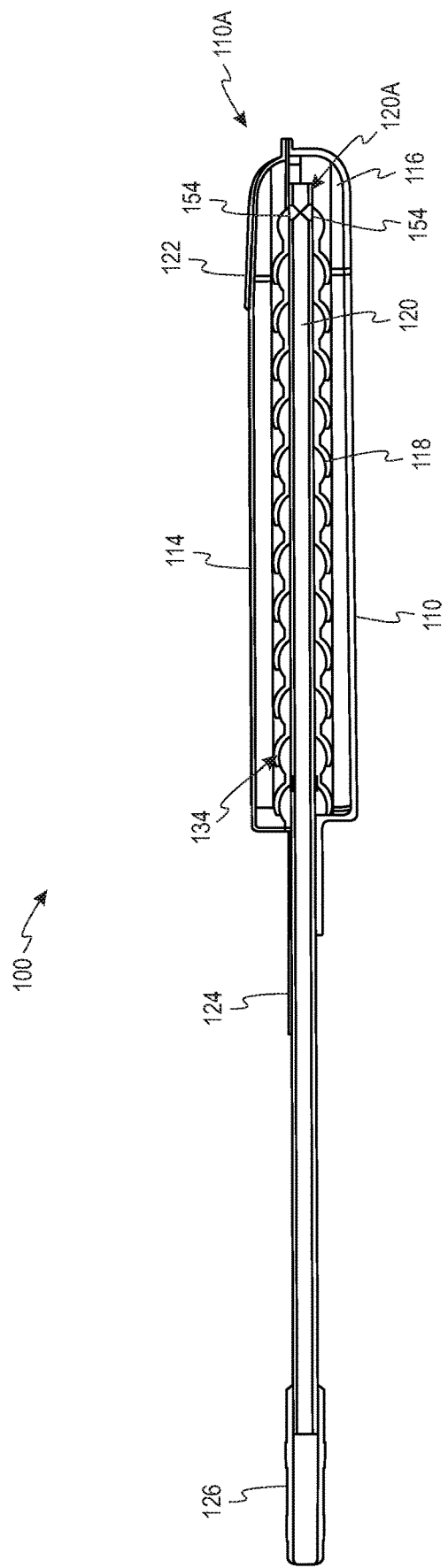
FIG. 1D depicts another cross-sectional view of the urine collection device shown in FIG. 1A.

1A depicts a perspective view of the urine collection device 100, FIG. 1B depicts an exploded view of the urine collection device 100, FIG. 1C depicts a first cross-sectional view of the urine collection device 100 through a line 1C-1C, and FIG. 1D depicts a second cross-sectional view of the urine collection device 100.

As shown in FIGS. 1A-1D, the urine collection device 100 includes a covering 110, a fluid collection assembly 112, and a top sheet 114. The fluid collection assembly 112 includes a foam sleeve 116, a shape retaining element 118, and a tube 120. Additionally, the urine collection device 100 can include a fluid-impermeable barrier 122, an anchor 124, and/or a suction adapter 126. These components of the urine collection device 100 will be further described below with respect to FIGS. 1A-1D and FIGS. 2-5C, which depict additional aspects of the components of the urine collection device 100 shown in FIGS. 1A-1D.

As shown in FIGS. 1A-1D and FIG. 2, the urine collection device 100 includes a covering 110 that defines a recessed receptacle 128. In general, the covering 110 can provide a fluid impermeable layer that can assist in retaining a fluid, such as urine, in the recessed receptacle 128. In one example, the covering 110 can be made from a foam material such as, for instance, a polymer foam, a fabric coated with a film, and/or an elastomeric polymer (e.g., silicone). Making the covering 110 from a foam material can beneficially provide for forming the covering 110 using a thermoforming process, which can help to improve manufacturing efficiency, improve manufacturing speed, improve manufacturing quality, and/or reduce manufacturing costs relative to other types of materials. However, in other examples, the covering 110 can be made from other materials and/or made by other manufacturing processes (e.g., vacuum forming, injection molding, and/or compression molding).

Figure 2:
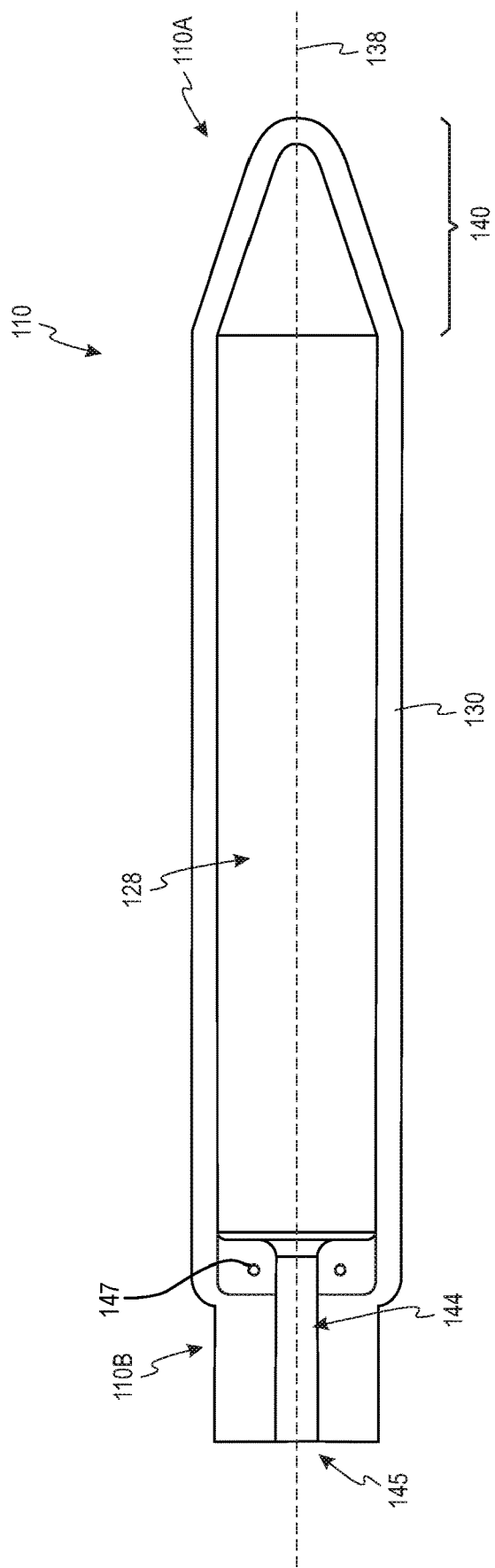
FIG. 2 depicts a covering of the urine collection device, according to an example.

As shown in FIGS. 1B and 2, the covering 110 includes an upper peripheral edge 130. The upper peripheral edge 130 can assist in coupling the covering 110 to the top sheet 114. In FIGS. 1B and 2, the upper peripheral edge 130 defines a flange portion extending outwardly in a plane away from the recessed receptacle 128. This can help to increase a surface area for coupling the covering 110 to the top sheet 114. However, in other examples, the upper peripheral edge 130 can omit the flange portion (i.e., the upper peripheral edge can be entirely coplanar with a wall of the recessed receptacle 128). This can reduce (or avoid) forming a seam 132 (shown in FIG. 1A) at an interface between the covering 110 and the top sheet 114.

In FIGS. 1A-1D, the top sheet 114 is coupled to the covering 110 at the upper peripheral edge 130. As examples, the top sheet 114 can be coupled to the covering 110 by heating sealing and/or welding (e.g., ultrasonic welding and/or radiofrequency welding) the top sheet 114 and the covering 110. The top sheet 114 can additionally or alternatively be coupled to the covering 110 by an adhesive. For instance, in one implementation, a relatively thin layer of film and/or adhesive (e.g., a polyurethane adhesive and/or a polyethylene adhesive) can be applied to the covering 110 to the covering 110 before or after forming the recessed receptacle 128 in the covering 110 (e.g., before or after thermoforming), and prior to coupling the top sheet 114 to the covering 110. In implementations in which the top sheet 114 is coupled to the covering 110 by the adhesive, welding, and/or heat sealing, the film and/or the adhesive can help to strengthen the coupling between the top sheet 114 and the covering 110 imparted by the heat sealing.

When the top sheet 114 is coupled to the covering 110, the top sheet 114 and the covering 110 define an internal chamber 134 of the urine collection device 100 as shown in FIG. 1D. In general, the top sheet 114 can draw fluids such as urine into the internal chamber 134 and toward the fluid collection assembly 112. For instance, the top sheet 114 can be formed of a material having a relatively high absorptive rate, a relatively high adsorption rate, and/or a relatively high permeation rate such that fluids such as urine can be rapidly wicked and drawn into the internal chamber 134 of the urine collection device 100 (and toward the fluid collection assembly 112). As one example, the top sheet 114 can be made from an absorbent polyester mesh material (e g a jersey mesh material) As another example, the top sheet 114 can be made of a blend of polyester and spandex (e.g., a blend including approximately 90 percent polyester and approximately 10 percent spandex). In yet another example, the top sheet 114 can include a fibrous material that is configured to draw the urine toward the fluid collection assembly 112 under capillary action. In another example, the top sheet 114 can be formed from a material having a total weight of approximately 4.0 ounces per square yard (plus or minus approximately 5%), a fiber that is a mechanically wicking yarn, a knit configured as a circular knit, a dimpled face, a wicking finish, and a width of approximately 60 inches to approximately 61 inches.

As shown in FIGS. 1A-1D, the urine collection device 100 can have a tapered section 136 at a distal end 100A of the urine collection device 100. For instance, in FIGS. 1B and 2, the upper peripheral edge 130 of the covering 110 tapers inwardly toward a center axis 138 of the covering 110 such that the covering 110 includes a tapered portion 140 at a distal end 110A of the covering 110. Similarly, as shown in FIGS. 1A-1D, the top sheet 114 can include a peripheral edge 142 that tapers inwardly in a manner similar to the tapered portion 140 of the covering 110. The tapered section 136 of the urine collection device 100, which is formed by the tapered portion 140 of the covering 110 and the tapered portion of the top sheet 114, can help to improve patient comfort and assist in retaining the urine collection device 100 at a desired position on a user. For instance, in an example, the tapered section 136 can be sized and/or shaped to fit into gluteal folds and a perineum of a body of the user such that the urine collection device 100 remains in a relatively fixed position on the body of the user.

Additionally, within examples, the tapered section 136 can be wedge shaped to assist in retaining the urine collection device 100 in the gluteal folds and/or the perineum of the user. For instance, the wedge shape of the tapered section 136 can define an edge at the distal end 100A, the edge can have a length and a width, and the length can be greater than the width.

In one example, the tapered section 136 can have a length of approximately 1 inch to approximately 2 inches. In another example, the tapered section 136 can have a length of approximately 1.75 inches. These example lengths can additionally or alternatively assist in retaining the tapered shape in the gluteal folds and/or the perineum of the user.

Additionally or alternatively, example materials described herein with respect to components of the urine collection device 100 at the distal end 100A can provide the tapered section 136 with a flexibility that allows the tapered section 136 to conform to a shape of the gluteal folds and/or the perineum of the user when the tapered section 136 is positioned in the gluteal folds and/or the perineum of the user.

In FIGS. 1A-1D, the fluid collection assembly 112 is in the internal chamber 134 of the urine collection device 100 between the covering 110 and the top sheet 114. Within examples, the recessed receptacle 128 of the covering 110 can facilitate positioning and retaining the fluid collection assembly 112 between the covering 110 and the top sheet 114 during a manufacturing process. In particular, the recessed receptacle 128 of the covering 110 can receive the fluid collection assembly 112. For instance, in FIGS. 1A-2, the recessed receptacle 128 can define a trough into which the fluid collection assembly 112 can be positioned. In one example, the recessed receptacle 128 of the covering 110 and the fluid collection assembly 112 can have respective sizes and/or shapes such that the covering 110 engages approximately 30 percent to approximately 70 percent of an outermost surface of the fluid collection assembly 112 (i.e., the outermost surface of the foam sleeve 116). In another example, the recessed receptacle 128 of the covering 110 and the fluid collection assembly 112 can have respective sizes and/or shapes such that the covering 110 engages at least approximately 50 percent of the outermost surface of the fluid collection assembly 112.

The relative sizes and/or shapes of the recessed receptacle 128 and the fluid collection assembly 112 can help manufacturing processes by assisting in retaining the fluid collection assembly 112 in a desired position relative to the covering 110 while one or more manufacturing operations are performed (e.g., such as coupling the top sheet 114 to the covering 110 and/or the manufacturing operations described below). The relative sizes and/or shapes of the recessed receptacle 128 and the fluid collection assembly 112 can additionally or alternatively help to provide the fluid impermeable layer of the covering 110 over a surface area that is suitable for retaining fluid, such as urine, within the urine collection device 100 during use.

As shown in FIGS. 1B and 2, the covering 110 can also include a channel 144 that extends from the recessed receptacle 128 to an opening 145 at a proximal end 110B of the covering 110. The upper peripheral edge 130 can extend continuously around a periphery of the covering 110, except at the opening 145. The channel 144 can receive the tube 120 to provide egress of fluid, such as urine, in a proximal direction out of the internal chamber 134. As shown in FIG. 1B, the channel 144 can have a depth that is less than a depth of the recessed receptacle 128. This can help to more closely conform the covering 110 to the fluid collection assembly 112 based on a position of the tube 120 in the fluid collection assembly 112 (i.e., the position of the tube 120 relative to the outermost surface of the foam sleeve 116).

Additionally, as shown in FIGS. 1C and 2, the covering 110 can include one or more vent apertures 147 extending through the covering 147 (e.g., in the recessed receptacle 128 adjacent to the proximal end 110B of the covering 110). The one or more vent apertures 147 can be configured to allow air to pass between the internal chamber 134 and an external environment in the event that the urine collection device 100. This can help to mitigate relatively high pressures being applied to the patient in the evet that the urine collection device 100 fully suctioned to the user. The one or more vent apertures 147 can be formed during or after forming the covering 110, and after placing the top sheet 114 (e.g., by mechanically punching the vent apertures 147 in the covering 110 and/or by laser cutting the vent apertures 147 in the covering 110). Although the urine collection device 100 includes two vent apertures 147 in the illustrated example, the urine collection device 100 can include a different quantity of vent apertures 147 in other examples (e.g., one vent aperture 147, three vent apertures 147, four vent apertures 147, etc.).

Figure 3:
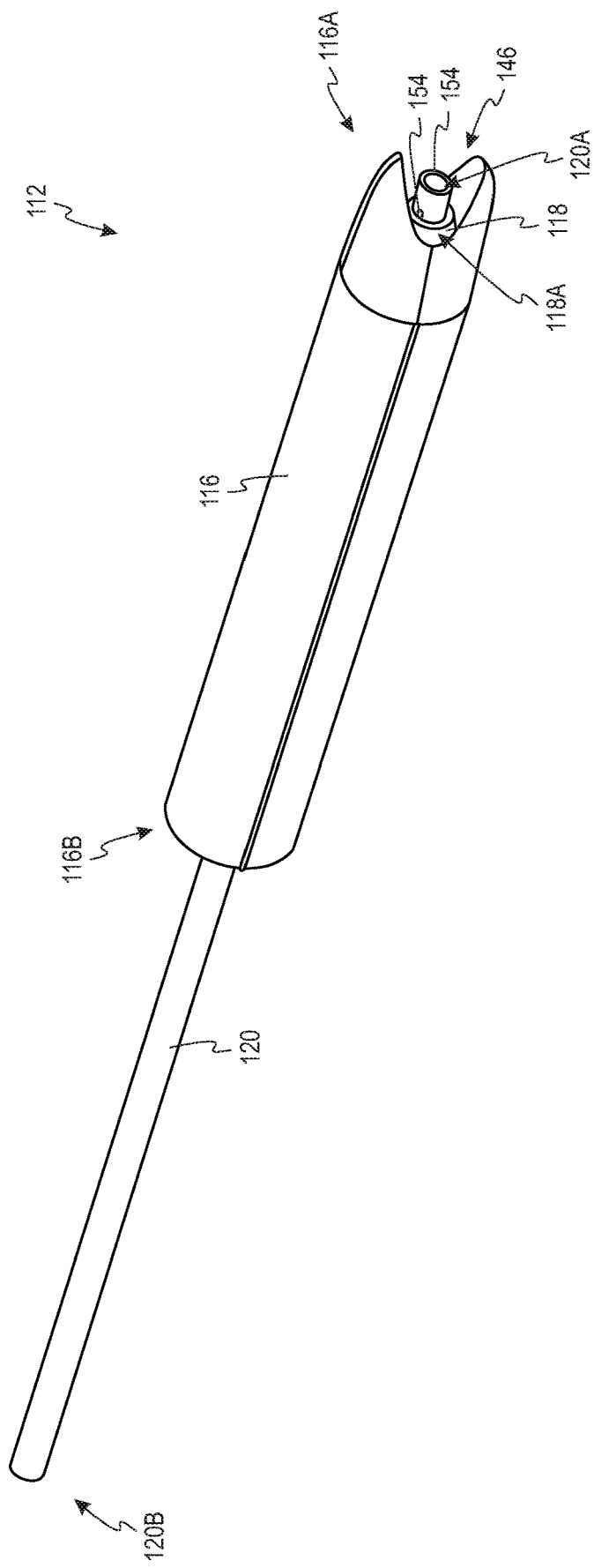
FIG. 3 depicts a fluid collection assembly of the urine collection device, according to an example.

As noted above, when the urine collection device 100 is assembled as shown in FIGS. 1A-1D, the fluid collection assembly 112 is positioned in the recessed receptacle 128 defined by the covering 110. FIG. 3 depicts the fluid collection assembly 112 including the foam sleeve 116, the shape retaining element 118, and the tube 120. As shown in FIGS. 1B and 3, the foam sleeve 116 includes a bore 146 extending from a first end 116A of the foam sleeve 116 to a second end 116B of the foam sleeve 116. The shape retaining element 118 is positioned in the bore 146 of the foam sleeve 116. The shape retaining element 118 defines a passage 148 extending from between a distal end 118A of the shape retaining element 118 and a proximal end 118B of the shape retaining element 118. The tube 120 extends through the passage 148 defined by the shape retaining element 118.

As shown in FIGS. 1C-1D, the foam sleeve 116 can help to reduce a contact pressure of the tube 120 and/or the shape retaining element 118 on a body of a user.

The foam sleeve 116 can be made from any suitable material and has suitable shape that allows for collecting fluid (e.g., urine) and/or directing fluid flow into the internal chamber 134 of the urine collection device 100. As one example, the foam sleeve 116 can be made from a reticulated foam material (e.g., VOLARA® Type EO foam, which is currently manufactured by Sekisui Voltek having a place of business in Lawrence, Mass.). In one implementation, the foam sleeve 116 can have a pore size between approximately 20 pores per inch (PPI) and approximately 90 PPI (e.g., approximately 45 PPI), a density between approximately 1.36 pounds per cubic feet and approximately 2.10 pounds per cubic feet (e.g., approximately 1.86 pounds per cubic feet), a tensile strength of at least approximately 20.0 pounds per square inch (PSI) (e.g., approximately 22.3 PSI), an elongation of at least approximately 240 percent (e.g., approximately 254 percent), a tear of at least approximately 3.5 pounds per inch (e.g., approximately 4.5 pounds per inch), a compression load deflection (CLD) 25% R of at least approximately 0.30 PSI (e.g., approximately 0.49 PSI), a CLD 65% R of at least approximately 0.50 PSI (e.g., approximately 0.96 PSI), and/or a compression set 50% of less than approximately 20 percent (e.g., approximately 4 percent).

In one example, the foam sleeve 116 can be formed by first positioning the shape retaining element 118 between a first sheet of foam and a second sheet of foam. After positioning the shape retaining element between the first sheet of foam and the second sheet of foam, the first sheet of foam can be coupled to the second sheet of foam on opposing sides of the shape retaining element. For instance, in one implementation, the first sheet of foam and the second sheet of foam can be heat sealed to each other (e.g., via a C-shaped heat sealing tool). After coupling the first sheet of foam to the second sheet of foam, cutting the first sheet of foam and the second sheet of foam on the opposing sides of the shape retaining element 118 to form the foam sleeve 116 with the shape retaining element 118 positioned in the bore 146 of the foam sleeve 116. This process can help to rapidly and/or efficiently manufacture the foam sleeve 116. However, in another example, the foam sleeve 116 can be formed by an extrusion process.

In FIGS. 1B-1D, the foam sleeve 116 can extend into the tapered section 136 of the urine collection device 100). For instance, as shown in FIG. 1C and FIG. 1D, the foam sleeve 116 extends into the tapered portion 140 at the distal end 110A of the covering 110 to a position proximate to and/or abutting with the distal end 110A of the covering 110. This can help to mitigate (or prevent) the urine collection device 100 collapsing at the distal end 100A and, thus, assist with retaining the urine collection device 100 at a desired position on a body of a user.

Figure 4A:
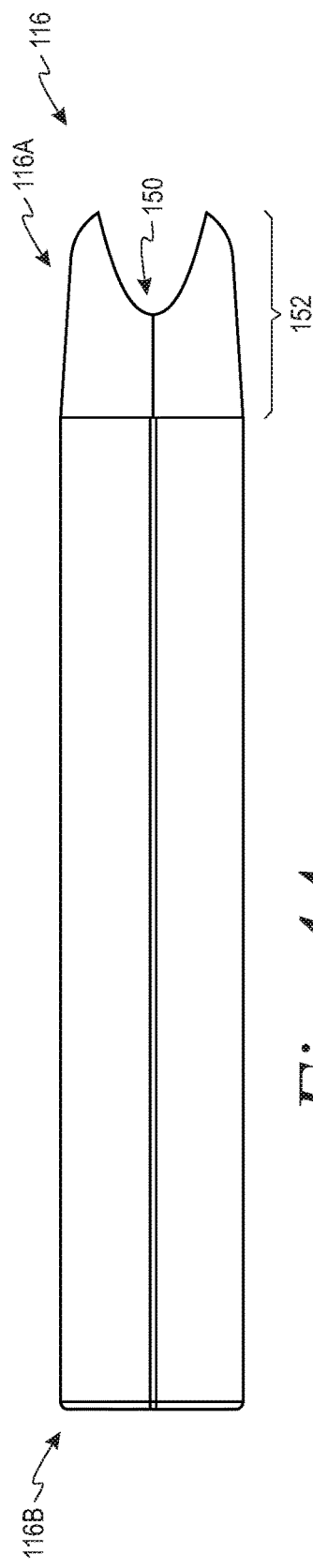
FIG. 4A depicts a first side view of a foam sleeve of the urine collection device, according to an example.
Figure 4B:
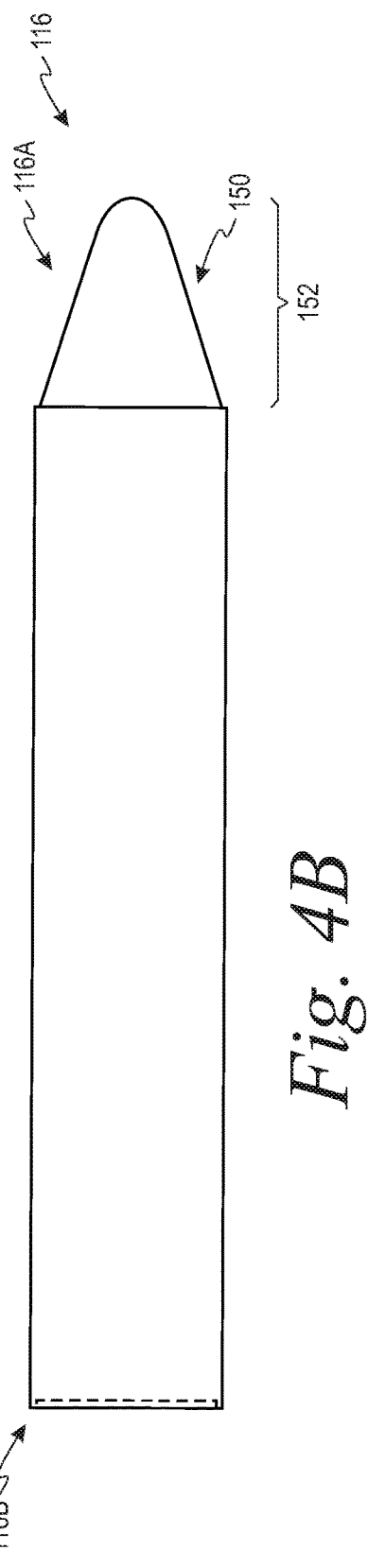
FIG. 4B depicts a second side view of a foam sleeve of the urine collection device, according to an example.
Figure 4C:
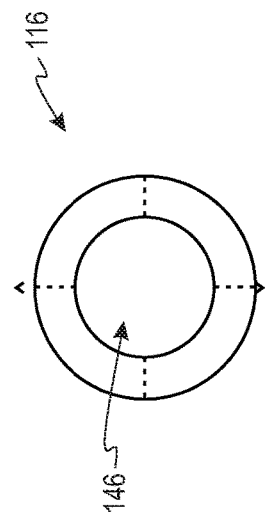
FIG. 4C depicts a third side view of a foam sleeve of the urine collection device, according to an example.

To facilitate positioning the foam sleeve 116 in the tapered portion 140 at the distal end 110A of the covering 110, the foam sleeve 116 can include a chamfer 150 at the tapered portion 140 of the covering 110. The chamfer 150 and the bore 146 of the foam sleeve 116 are further shown in FIGS. 4A-4C. FIG. 4A depicts a side view of the foam sleeve 116, FIG. 4B depicts a top view of the foam sleeve 116, and FIG. 4C depicts a plan view of the first end 116A of the foam sleeve 116. As shown in FIGS. 4A-4B, the chamfer 150 can reduce a size of the foam sleeve 116 such that the foam sleeve 116 can fit in the tapered portion 140 of the covering 110.

The shape retaining element 118 is configured to conform the fluid collection assembly 112 to a curved configuration for placement against a body of a user and maintain the curved configuration of the fluid collection assembly 112 until the curved configuration is adjusted. This can help to adjust a shape of the urine collection device 100 based on a shape of the user's anatomy and thereby improve collecting and diverting urine from the user into the internal chamber 134 of the urine collection device 100. The shape retaining element 118 can additionally or alternatively facilitate adjusting the shape of the urine collection device 100 based on a shape of the user's anatomy to improve user comfort.

In one example, the shape retaining element 118 can include a plurality of linking segments 152 that are moveably coupled to each other. For instance, FIG. 5A depicts the shape retaining element 118 including the linking segments 152, FIG. 5B depicts a representative one of the linking segments 152, and FIG. 5C depicts a cross-sectional view of the linking segment 152 in FIG. 5B according to an example. As shown in FIG. 5A, the linking segments 152 are arranged sequentially along a longitudinal direction of the shape retaining element 118. As shown in FIGS. 5A-5C, each of the linking segments 152 has a first portion 152A, a second portion 152B, and a third portion 152C. Each of the first portion 152A, the second portion 152B, and the third portion 152C is hollow or has at least an open portion for passing the tube 120 therethrough. The first portion 152A includes a spherically shaped body with an opening therein. The first portion 152A is connected to a second portion 152B having a cylindrical shape and a passage therethrough for passing the tube 120. The second portion 152B is connected to the third portion 152C having a semi-spherical shape and forming a hollow cup. The first portion 152A (the spherical shape) of one segment 152 is configured to fit within the hollow cup of the third portion 152C of an immediately successive segment 152.

In this way, the linked segments 152 include a series of individual segments linked to (e.g., by snapping together) a successive individual segment, wherein each segment 152 is moveable relative to the successive segment as the first portion 152A moves within the hollow cup of the third portion 152C. Further, the shape retaining element 118 can be manipulated by a person (e.g., a healthcare provider or a user) in various directions and is configured to retain its shape following the manipulation. As such, a curvature of urine collection device 100 is adjustable, for example, to fit the anatomical curvature of a particular user.

The linking segments 152 can collectively define the passage 148 extending between the distal end 118A and the proximal end 118B of the shape retaining element 118. As shown in FIGS. 1C, 1D, and 3, the tube 120 extends through the passage 148 defined by the shape retaining element 118.

The tube 120 is configured to allow a vacuum (e.g. a pressure lower than ambient air pressure) to be produced in the internal chamber 134 of the urine collection device 100 when suction is applied to the tube 120. In this way, fluid (e.g.; urine) collected in the internal chamber 134 of the urine collection device 100 can be evacuated from the urine collection device 100 through the tube 120.

As shown in FIGS. 1A and 1C-1D, the tube 120 includes a distal end 120A in the internal chamber 134 at the distal end 100A of the urine collection device 100 and a proximal end 120B that extends proximally from the internal chamber 134 at the proximal end 100B of the urine collection device 100. More specifically, as shown in FIGS. 1C-1D, the tube 120 extends distally from the shape retaining element 118 into the tapered portion 140 at the distal end 110A of the covering 110. In this way, the tube 120 can be in fluid communication with the distal end 100A of the urine collection device 100. As such, when fluid (e.g., urine) is received in the internal chamber 134, the fluid can flow down (e.g., under gravity and/or vacuum pressure) and enter the distal end 120A of the tube 120.

As shown in FIGS. 1B-1D and 3, the tube 120 can include a plurality of apertures 154 at a distal portion of the tube 120. Providing a plurality of apertures 154 at the distal portion of the tube 120 can help to enhance air flow into the tapered section 136 at the distal end 110A of the urine collection device 100 and/or inhibit (or prevent) a vacuum lock, which would prevent the flow of fluid (e.g., urine) through the tube 120.

Additionally, as shown in FIGS. 1C-1D and 3, the distal end 120A of the tube 120 can be approximately flush with the first end 116A of the foam sleeve 116. In FIG. 3, the distal end 118A of the shape retaining element 118 is located proximal to the distal end 120A of the tube 120. This can help to expose the apertures 154 to enhance air flow and/or receive fluid into the tube 120. In one example, the distal end 118A of the shape retaining element 118 can be approximately 0.25 inches from the distal end 120A of the tube 120.

Within examples, the tube 120 can be a flexible material to facilitate directing the tube 120 away from the user's body. It can be beneficial to direct the tube 120 away from the user's body (e.g., off the side of a bed) to reduce (or prevent) the tube 120 from accidental pulling and leakage resulting from such pulling (e.g., due to the tube 120 accidentally decoupling from another drain tube at the suction adapter 126). This may also be beneficial in that the tube 120 can be routed to either side of the bed and this can provide greater flexibility in positioning additional equipment (e.g., the equipment described below with respect to FIG. 6) relative to the user. Additionally, in implementations in which the suction adapter 126 is made of a relatively hard material (e.g., a relatively hard plastic), directing the tube 120 and the suction adapter 120 away from the user's body can enhance user comfort.

As examples, the tube 120 can have a length that is greater than approximately six inches. Additionally, in one example, the tube 120 can have a durometer of approximately 72 Shore A, an inner diameter of approximately 0.170 inches, and an outer diameter of approximately 0.253 inches. These example durometer and dimension parameters of the tube 120 can achieve the benefits associated with the flexibility of the tube 120 described above. However, the tube 120 can have a different hardness and/or different dimensions in other examples. For instance, the tube 120 can have a durometer between approximately 50 Shore A and approximately 100 Shore A in another example.

In another example, the tube 120 can have a kink distance of approximately 1 as determined in accordance with a test conducted in accordance with the standard provided by "BS EN 13868:2002 Catheters—Test methods for kinking of single lumen catheters and medical tubing". In another example, the tube 120 can have a kink distance less than approximately 2 as determined in accordance with a test conducted in accordance with the standard provided by "BS EN 13868:2002 Catheters—Test methods for kinking of single lumen catheters and medical tubing". In yet another example, the tube 120 can have a kink distances less than approximately 3 as determined in accordance with a test conducted in accordance with the standard provided by "BS EN 13868:2002 Catheters—Test methods for kinking of single lumen catheters and medical tubing". As noted above, the urine collection device 100 can also include a suction adapter 126. The suction adapter 126 can include a stepped tapering to help couple the tube 120 to a suction tube of a vacuum device. Providing the suction adapter 126 with a shape that tapers inwardly along a direction from the distal end 110A toward the proximal end 100B can help to couple the suction adapter 126 with a relatively wide variety of different tubes (e.g., a drain tube as described below with respect to FIG. 6) having differently sized tube diameters. As such, the tapered shape of the suction adapter 126 can help to make the urine collection device 100 more universally compatible with other equipment in a healthcare environment. In other examples, the suction adapter 126 can additionally or alternatively include a thread, a hose barb, and/or a Luer lock for coupling with the tube of the suction tube of the vacuum device.

Although the suction adapter 126 is shown in FIGS. 1A-1D as a male-type component that is configured to be received by a female-type component (e.g., an open end of a drain tube), the suction adapter 126 can alternatively be provided as a female-type component that is configured to couple with a male-type component of other equipment in a healthcare environment. For example, the suction adapter 126 can include a socket in which a male-type adapter of a drain tube can be inserted and retained.

Additionally, as noted above, the urine collection device 100 can also include a fluid-impermeable barrier 122. As shown in FIG. 1A, the fluid-impermeable barrier 122 is coupled to a distal portion of the covering 110 (e.g., at the tapered portion 140 of the covering 110). The fluid-impermeable barrier 122 and the distal portion of the covering 110 can define a fluid-impermeable chamber. In this way, the fluid-impermeable barrier 122 can assist in retaining the fluid (e.g., urine) in the internal chamber 134 of the urine collection device 100. Additionally or alternatively, the fluid-impermeable barrier 122 can help to provide a barrier against fecal contamination.

As examples, the fluid-impermeable barrier 122 can be made from a fluid-impermeable material such as, for instance, a foam, silicone, urethane, and/or other types of impermeable elastomeric polymers. In some implementations, the fluid-impermeable barrier 122 can be made from a material that is the same as a material of the covering 110. In other implementations, the fluid-impermeable barrier 122 can be made from a material that is different than a material of the covering 110.

As shown in FIG. 1A, the anchor 124 is coupled to a proximal portion of the covering 110. The anchor 124 includes an adhesive configured to couple the urine collection device 100 to the user. In this way, the anchor 124 is configured to secure the urine collection device 100 to the user in a position in which the urine collection device 100 can collect and divert the fluid (e.g., urine) into the internal chamber 134 of the urine collection device 100.

Within examples, the anchor 124 can have a shape that can conform to a surface area of a pelvic region of the user without pulling or pinching the skin or otherwise causing discomfort. The anchor 124 can have any suitable shape for securing the urine collection device 100 to the body of a user (e.g., and remain secured to the user despite motion by the user, moisture accumulation on the body, and/or passage of time).

In FIGS. 1A-1D, the anchor 124 includes a first arm 124A and a second arm 124B laterally extending from a center portion 124C. In this arrangement, when the anchor 124 is secured to the user via the adhesive, the center portion 124C can be located at a middle area of the user's pelvic area and/or abdomen so that the first arm 124A and the second arm 124B extend to areas adjacent to the middle area of the user's pelvic area and/or abdomen. This can help to improve stability of the urine collection device 100 secured to the user.

In one example, the first arm 124A and the second arm 124B can include the adhesive, whereas the center portion 124C can omit the adhesive. This can additionally or alternatively assist in reducing (or minimizing) an extent to which the adhesive adheres to hair of the user. Omitting the adhesive at the center portion 124C also can be beneficial for users that do not have hair at the middle area of the user's pelvic area and/or abdomen as omitting the adhesive at the center portion 124C reduces an amount of adhesive on the user's skin and, thus, improves patient comfort. In one implementation, the center portion 124C omitting the adhesive can be, for instance, approximately 1.6 inches wide.

In another example, the first arm 124A, the second arm 124B, and the center portion 124C can include the adhesive such that the adhesive can adhere to the user at the first arm 124A, the second arm 124B, and/or the center portion 124C of the anchor 124. In these examples, the anchor 124 can include a liner that can initially cover the adhesive prior to coupling the anchor 124 to the user, and be removed to expose the adhesive to facilitate coupling the anchor 124 to the user.

In some examples, the tube 120 can be coupled to the anchor 124. This can help to mitigate (or prevent) the tube 120 from migrating from a desired position in the internal chamber 134 relative to the distal end 110A of the covering 110. In other examples, the tube 120 can be additionally or alternatively coupled to the shape retaining element 118.

Figure 6:
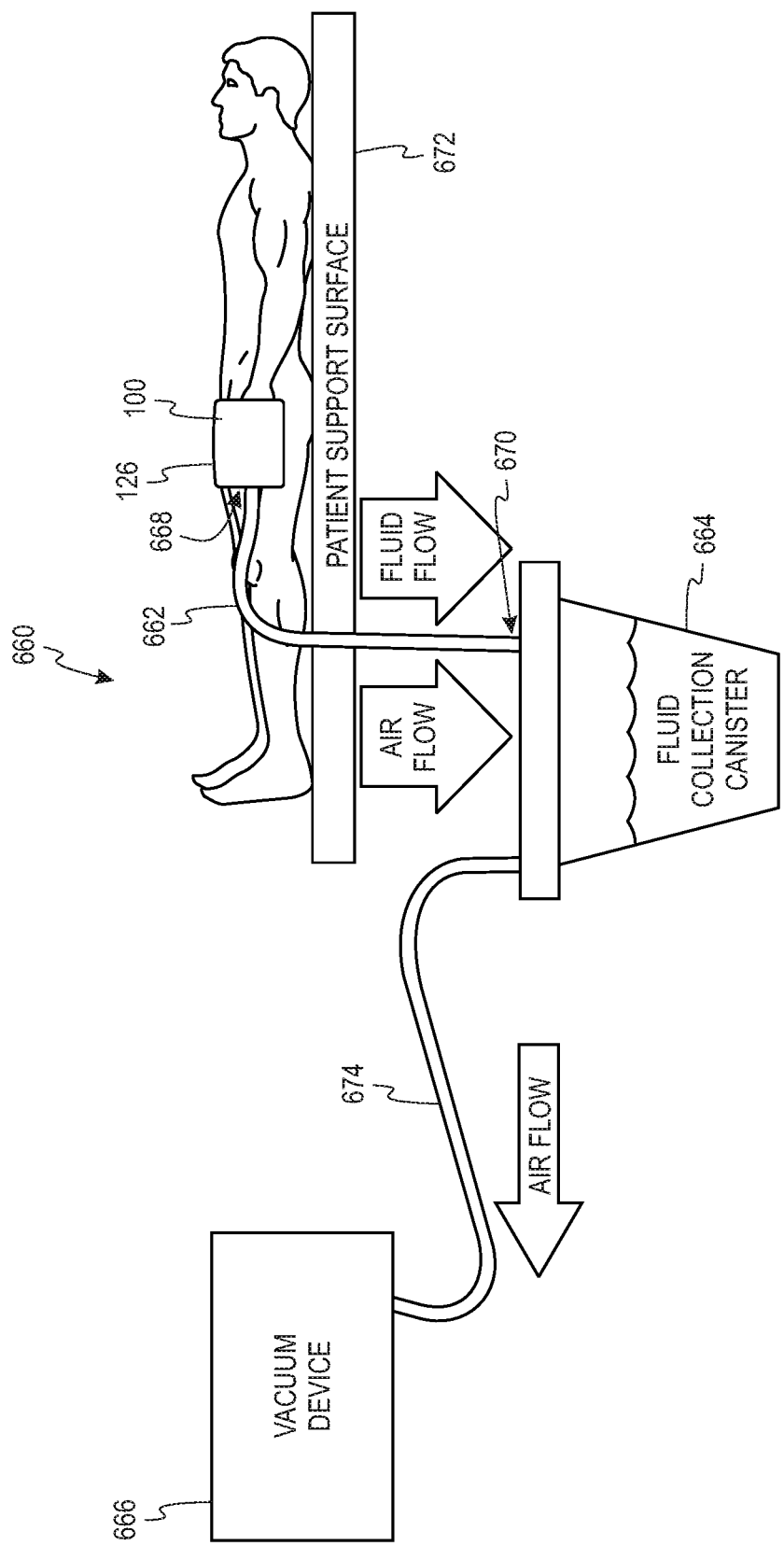
FIG. 6 depicts a system for collecting urine according to an example.

Referring now to FIG. 6, a simplified diagram of a system 660 for collecting urine is depicted according to an example embodiment. As shown in FIG. 6, the system 660 includes the urine collection device 100 described above. Additionally, the system 660 includes a drain tube 662, a waste collection reservoir 664, and a vacuum device 666.

A first end 668 of the drain tube 662 is coupled to the suction adapter 126 of the urine collection device 100. For example, the drain tube 662 can include a thread, a Luer lock, and/or other feature for coupling the drain tube 662 to the suction adapter 126. Within examples, the drain tube 662 can be a flexible material to facilitate directing the drain tube away from the user's body. It can be beneficial to direct the drain tube 662 away from the user's body (e.g., off the side of a bed) to reduce (or prevent) the drain tube 662 from accidental pulling and leakage resulting from such pulling.

The waste collection reservoir 664 is coupled to a second end 670 of the drain tube 662 to receive the urine from the drain tube 662. In one example, the waste collection reservoir 664 can be a leg bag, a drainage bag, or other container.

In another example, the waste collection reservoir 664 can include a hanger and/or another structure for coupling the waste collection reservoir 664 to a patient support surface 672 (e.g., a bed and/or a wheelchair) used by the patient.

In some examples, the waste collection reservoir 664 can be a sealed container. This can, for example, reduce (or minimize) a risk of spillage and/or contamination. In some examples, the waste collection reservoir 664 can be disposable. In other examples, the waste collection reservoir 664 can be reusable. For instance, the waste collection reservoir 664 can be configured to be sterilized after a use and reused.

The vacuum device 666 can apply a vacuum pressure to the drain tube 662 to assist in directing the urine from the suction adapter 126 to the waste collection reservoir 664. For instance, the vacuum device 666 can include an air pump or other vacuum source, which is coupled to the waste collection reservoir 664 by an air tube 674. In one example, the air tube 674 can also be made of a flexible material.

In some examples, the vacuum device 666 can be a wall vacuum integrated into a room of a medical facility. In other examples, the vacuum device 666 can be integrated with the patient support surface 672. For instance, the vacuum device 666 can be integrated with a bed in a medical facility.

Within some examples, the system can also include an occlusion clip for selectively controlling the flow of urine in the drain tube. For instance, the occlusion clip can provide for stopping the flow of urine in the drain tube to facilitate changing and/or emptying the waste collection reservoir.

In use, the urine collection device 100 can be attached to the user. For example, the urine collection device 100 can be against the body of the user with the top sheet 114 in operative relation with a urethral opening of the user. In an example, this can include positioning the urine collection device 100 in a vertical orientation relative to a urethral opening of a female user. Additionally, positioning the urine collection device 100 relative to the user can include adjusting a curvature of the urine collection device 100 (e.g., by bending the shape retaining element 118) to conform a shape of the urine collection device 100 to a shape of the user.

After positioning the urine collection device 100 relative to the user, the urine collection device 100 can be secured to the user with an adhesive on an anchor 124 of the urine collection device 100. Additionally or alternatively, the urine collection device 100 can be secured to the user by engaging the distal end 100A of the urine collection device 100 (i.e., the tapered section 136) with a portion of the user's anatomy.

The drain tube 662 can be coupled to the suction adapter 126 at the first end 668 and the waste collection reservoir 664 at the second end 670. The vacuum device 666 can also be connected to the waste collection reservoir 654 by the air tube 674. The vacuum device 666 can then be operated to apply the vacuum pressure at the suction adapter 126 (e.g., via the air tube 674, the waste collection reservoir 664, and the drain tube 662).

In this arrangement, the urine collection device 100 can receive, through the top sheet 114 and by the fluid collection assembly 112, urine discharged from the urethral opening of the user. The urine can flow through the foam sleeve 116 and toward the distal end 120A of the tube 120. The urine can then be evacuated from the fluid collection assembly 112 through the tube 120.

Referring now to FIGS. 7A-7H, a process for manufacturing the urine collection device 100 is shown according to an example. As shown in FIG. 7A, the recessed receptacle 128 can be formed in a sheet of foam to form the covering 110. In one example, a thermoforming machine can apply thermal energy while pressing the sheet of foam into a mold in the shape of the recessed receptacle 128 to form the covering 110. In FIG. 7A, the sheet of foam includes a single recessed receptacle 128. However, in other examples, the thermoforming machine can form a plurality of recessed receptacles 128 in the sheet of foam and the sheet of foam can remain uncut between the recessed receptacles 128. This can help to more rapidly and/or efficiently manufacture a plurality of urine collection devices 100 by providing for simultaneous performance one or more operations of the manufacturing process described herein on the urine collection devices 100.

The process can also include inserting the tube 120 in the passage 148 of the shape retaining element 118. For instance, FIG. 7B shows the tube 120 inserted in the passage 148 of the shape retaining element 118. As shown in FIG. 7B, the distal end 120A of the tube 120 extends distally past the distal end 118A of the shape retaining element 118. Additionally, in FIG. 7B, the suction adapter 126 is coupled to the proximal end 120B of the tube 120.

To assemble the fluid collection assembly 112, the shape retaining element 118 and the tube 120 are positioned in the bore 146 of the foam sleeve 116 as shown in FIG. 7C. In one example, this can include positioning the shape retaining element 118 and the tube 120 between a first sheet of foam and a second sheet of foam and then coupling the first sheet of foam to the second sheet of foam on opposing sides of the shape retaining element 118 and the tube 120. For instance, in one implementation, a heat sealer machine can apply thermal energy and/or pressure to the first sheet of foam and the second sheet of form on the opposing sides of the shape retaining element 118 and the tube 120 to form a heat seal. The heat sealer can include, for example, a C-shaped tool to form the heat seal on the opposing sides of the shape retaining element 118 and the tube 120. After coupling the first sheet of foam to the second sheet of foam, a machine can cut the first sheet of foam and the second sheet of foam on the opposing sides of the shape retaining element to form the foam sleeve 116 with the shape retaining element 118 positioned in the bore 146 of the foam sleeve 116 and the tube 120 positioned in the passage 148 of the shape retaining element 118.

As shown in FIG. 7D, after forming the recessed receptacle 128 in the covering 110 and forming the fluid collection assembly 112, the fluid collection assembly 112 can be positioned in the recessed receptacle 128 of the covering 110. Also, as shown in FIG. 7D, the tube 120 can be positioned in the channel 144 of the covering 110 such that the tube 120 extends proximally from the covering 110.

After positioning the fluid collection assembly 112 in the recessed receptacle 128 of the covering 110, the top sheet 114 can be positioned on the covering 110 and the fluid collection assembly 112 such that the fluid collection assembly 112 is between the covering 110 and the top sheet 114 as shown in FIG. 7E. In FIG. 7E, the fluid-impermeable barrier 122 is coupled to the top sheet 114 prior to positioning the top sheet 114 on the covering 110 and the fluid collection assembly 112. For example, the fluid-impermeable barrier 122 can be coupled to the top sheet 114 by an adhesive, welding the fluid-impermeable barrier 122 to the top sheet 114, and/or melting the fluid-impermeable barrier 122 into the top sheet 114.

In this example, the fluid-impermeable barrier 122 overlaps a portion of the top sheet 114. However, in another example, the fluid-impermeable barrier 122 can extend from the top sheet 114 such that the fluid-impermeable barrier 122 dos not overlap with the top sheet 114 (e.g., the top sheet 114 may be omitted at the tapered portion 140 of the covering 110.

After positioning the top sheet 114 on the covering 110 and the fluid collection assembly 112, the top sheet 114 can be coupled to the covering 110 as shown in FIG. 7F. For example, a heat sealing machine can apply thermal energy and/or pressure to the top sheet 114 and the covering 110 (e.g., at the upper peripheral edge 130 shown in FIG. 1B) to heat seal the top sheet 114 to the covering 110. The top sheet 114 and the covering 110 can then be cut to form the seam 132 around the periphery of the urine collection device 100 at an interface between the covering 110 and the top sheet 114.

In this example, because the fluid-impermeable barrier 122 is coupled to the top sheet 114 prior to coupling the top sheet 114 to the covering 110, the process of coupling the top sheet 114 to the covering 110 simultaneously couples the fluid-impermeable barrier 122 to the covering 110.

Additionally, as noted above, the upper peripheral edge 130 defines a flange portion extending outwardly in a plane away from the recessed receptacle 128. This can help to increase a surface area for coupling the covering 110 to the top sheet 114 (e.g., at the peripheral edge 142 of the top sheet 114). Additionally, the upper peripheral edge 130 of the covering 110 and the peripheral edge 142 of the top sheet 114 can help to inhibit leakage. For instance, when urine is applied to a central area of the top sheet 114 and the foam sleeve 116 at a rate that exceeds a rate of absorption for the top sheet 114 and the foam sleeve 116, the excess urine waiting to be absorbed may spread out toward the upper peripheral edge 130 and the peripheral edge 142. The upper peripheral edge 130 and the peripheral edge 142 can act as gutters that direct the excess urine down toward less saturated portions of the top sheet 114 and the foam sleeve 116 and toward the distal end 120A of the tube 120 where the urine can be suctioned. In this way, the upper peripheral edge can inhibit (or prevent) the urine from leaking off the sides.

In one example, the upper peripheral edge 130 and the peripheral edge 142 can have a width of approximately 0.1875 inches to provide the gutter function for directing the urine down toward the distal end 120A of the tube 120. Additionally, as noted above, the top sheet 114 and the foam sleeve 116 can extend downward to the distal end 120A of the tube 120, which can help to direct the urine to the position at which it can be more effectively suctioned away from the urine collection device 100.

In an example implementation, the upper peripheral edge 130 and/or the peripheral edge 142 can form a slightly concave shape to help provide the gutter function (e.g., the concavity can face the user). For instance, the top sheet 114 can be kept under tension before sealing the upper peripheral edge 130 and the peripheral edge 142 such that the top sheet 114 pulls the upper peripheral edge 130 and the peripheral edge 142 inward once the profile of the urine collection device 100 is cut.

As shown in FIG. 7G, the anchor 124 can be coupled to the covering 110 at the proximal end 110B of the covering 110. In an example, the anchor 124 can be coupled to the covering 110 by an adhesive. Also, in some examples, the anchor 124 can additionally be coupled to the tube 120 to help mitigate (or prevent) movement of the tube 120 in an axial direction relative to the covering 110. In this arrangement, the tube 120 can be adhered to the covering 110 and/or the top sheet 114 such that the tube 120 is sandwiched between (i) the covering 110 and/or the top sheet 114, and (ii) the anchor 124. As shown in FIG. 7H, the process can result in the urine collection device 100 described above according to an example.

Additionally, in the example described above, the one or more vent apertures 147 can be formed during or after forming the covering 110, and after placing the top sheet 114 (e.g., by mechanically punching the vent apertures 147 in the covering 110 and/or by laser cutting the vent apertures 147 in the covering 110).

In the example described above, the fluid-impermeable barrier 122 is coupled to the top sheet 114 prior to coupling the top sheet 114 to the covering 110. Additionally, in the example illustrated in FIGS. 1A and 7H, the fluid-impermeable barrier 122 is co-extensive with the top sheet 114 on lateral sides of the urine collection device 100 (i.e., the fluid-impermeable barrier 122 does not extend past the top sheet 114 to overlap with portions of the covering 110 that are not overlapped by the top sheet 114). However, in another example, the fluid-impermeable barrier 122 can be coupled to top sheet 114 and the covering 110 after the top sheet 114 is coupled to the covering 110, and/or the fluid-impermeable barrier 122 can extend past the top sheet 114 to wrap substantially around the covering 110.

Figure 8:
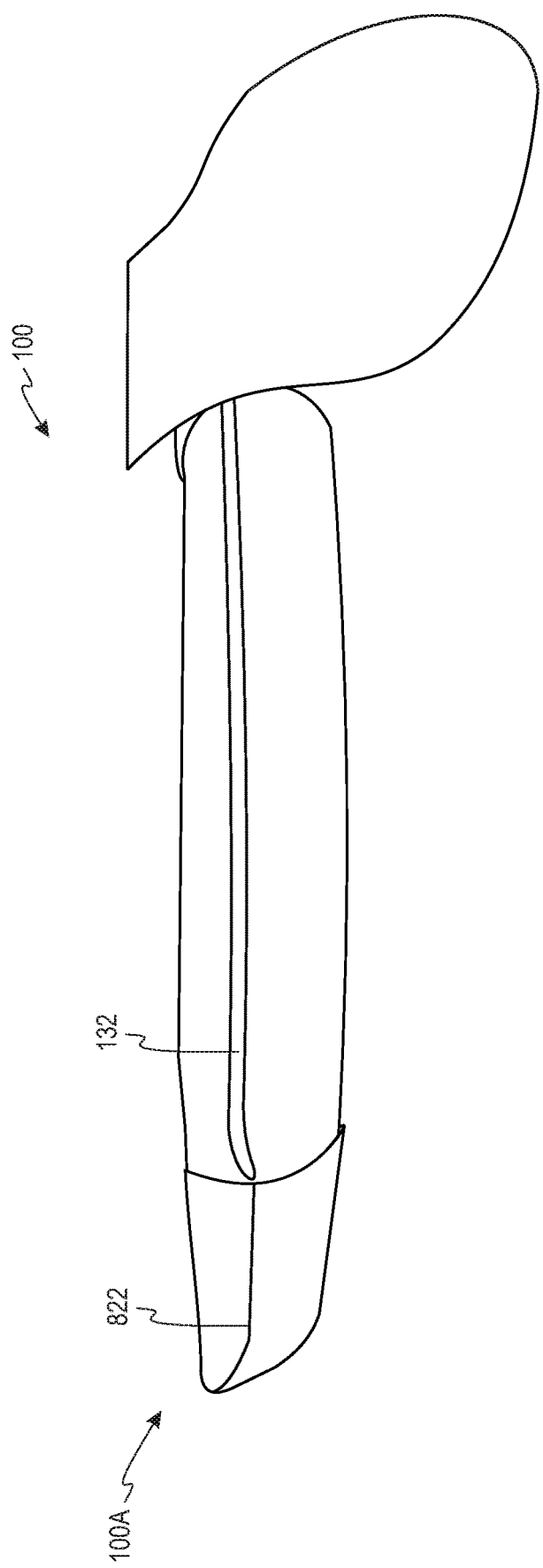
FIG. 8 depicts a urine collection device, according to another example.

As an example, FIG. 8 depicts the urine collection device 100, except with a fluid-impermeable barrier 822 instead of the fluid-impermeable barrier 122 shown in FIGS. 1A and 7H. As shown in FIG. 8, the fluid-impermeable barrier 822 wraps around the distal end 100A of the urine collection device 100 such that the fluid-impermeable barrier 822 covers the seam 132 at the distal end 100A. Covering the seam 132 at the distal end 100A with the fluid-impermeable barrier 822 can help to improve patient comfort.

Figure 9:
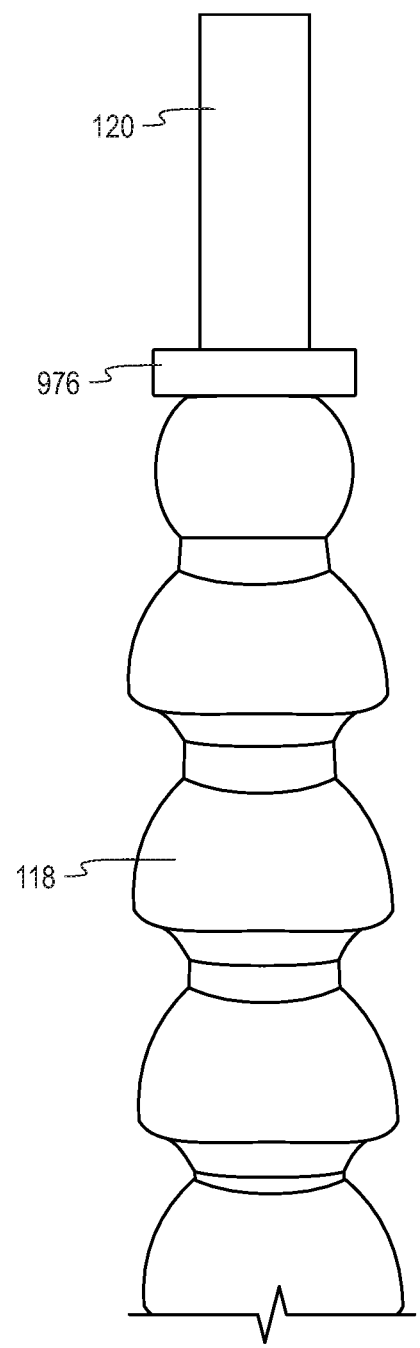
FIG. 9 depicts a urine collection device, according to another example.

Additionally, in the examples described above, the tube 120 can be coupled to the anchor 124 and/or the shape retaining element 118 to help (or prevent) the tube 120 from migrating from a desired position in the internal chamber 134 relative to the distal end 110A of the covering 110. In another example, the tube 120 can be additionally or alternatively coupled to another component of the urine collection device 100 to help maintain the position of the tube 120. For instance, FIG. 9 depicts an example in which the urine collection device 100 further includes a retention collar 976 coupled to the tube 120 to help maintain the position of the tube 120. As shown in FIG. 9, the retention collar 976 can be located adjacent to the distal end 120A (shown in FIG. 1B) of the tube 120 and have a size that is greater than a size of the passage 148 (shown in FIG. 1B) defined by the shape retaining element 118 (e.g., the retention collar 976 can be a flange that extends outwardly from the tube 120). In this arrangement, when the tube 120 is positioned in the passage 148 of the shape retaining element 118, the retention collar 976 can engage the shape retaining element 118 (i.e., as a stop) to inhibit or prevent proximal movement of the tube 120 relative to the shape retaining element 118.

Figure 10:
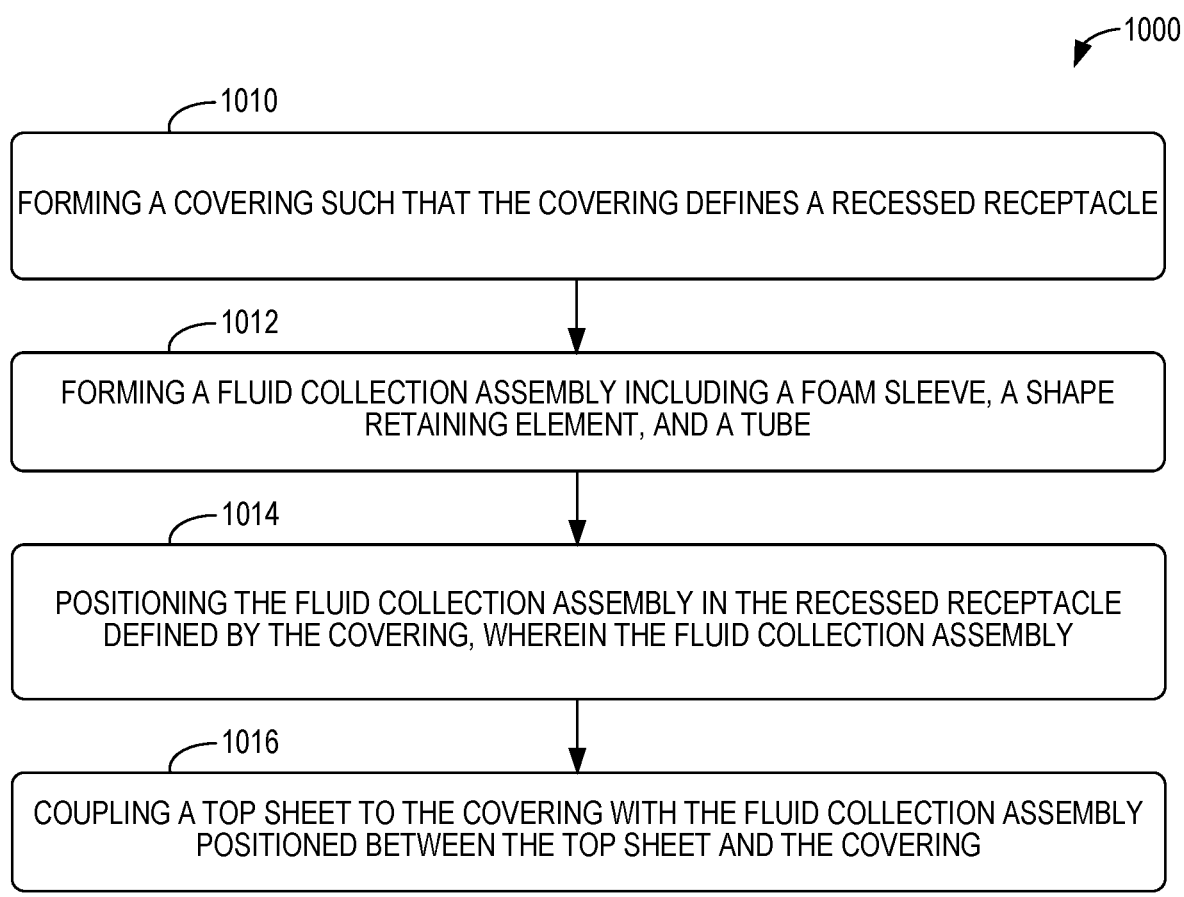
FIG. 10 depicts a flowchart for a process for making a urine collection device, according to an example.

Referring now to FIG. 10, a flowchart for a process 1000 of making a urine collection device is shown according to an example. As shown in FIG. 10, at block 1010, the process 1000 includes forming a covering such that the covering defines a recessed receptacle. At block 1012, the process 1000 includes forming a fluid collection assembly including a foam sleeve, a shape retaining element, and a tube.

The foam sleeve includes a bore extending from a first end of the foam sleeve to a second end of the foam sleeve. The shape retaining element is positioned in the bore of the foam sleeve. The shape retaining element is configured to conform the fluid collection assembly to a curved configuration for placement against a body of a user and maintain the curved configuration of the fluid collection assembly until the curved configuration is adjusted. The shape retaining element defines a passage extending from between a proximal end of the shape retaining element and a distal end of the shape retaining element. The tube extends through the passage defined by the shape retaining element.

Figure 11:
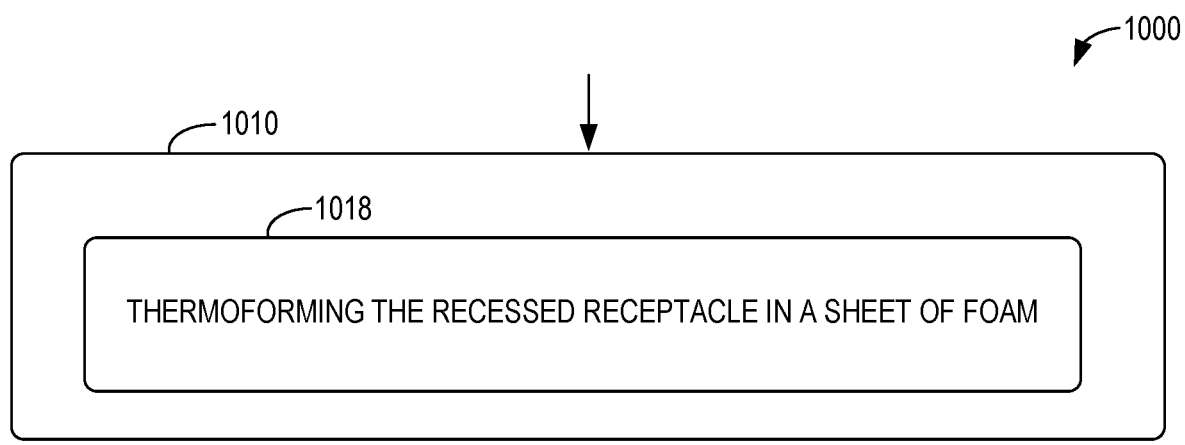
FIG. 11 depicts a flowchart for a process for making a urine collection device for use with the process shown in FIG. 10.

At block 1014, the process 1000 includes positioning the fluid collection assembly in the recessed receptacle defined by the covering, wherein the fluid collection assembly. At block 1016, the process 1000 includes coupling a top sheet to the covering with the fluid collection assembly positioned between the top sheet and the covering. The top sheet and the covering define an internal chamber of the urine collection device. The top sheet is configured to draw urine into the internal chamber and toward the fluid collection assembly FIGS. 11-21 depict additional aspects of the process 1000 according to further examples. As shown in FIG. 11, forming the covering at block 1010 can include thermoforming the recessed receptacle in a sheet of foam at block 1018.

Figure 12:
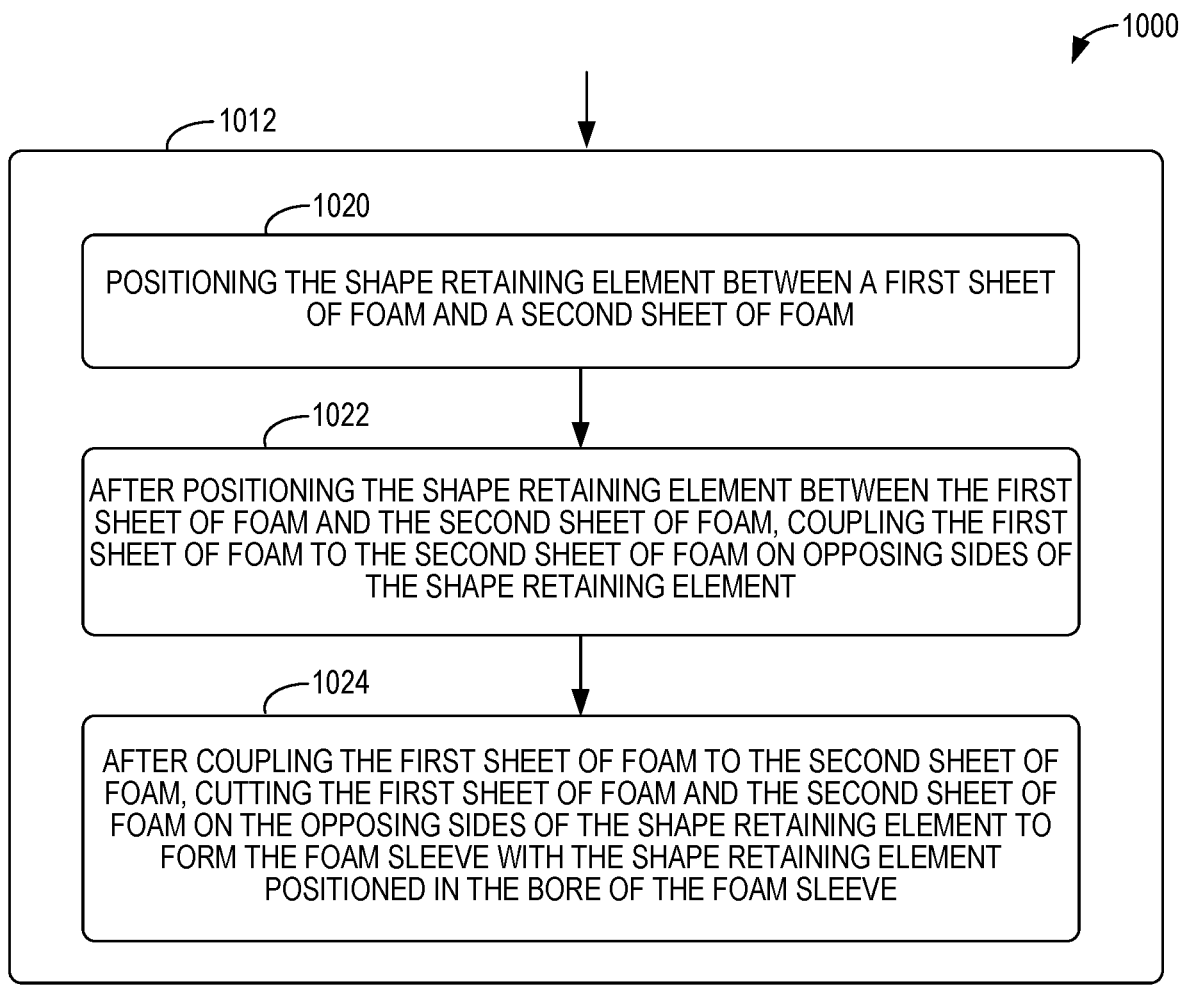
FIG. 12 depicts a flowchart for a process for making a urine collection device for use with the process shown in FIG. 10.

As shown in FIG. 12, forming the fluid collection assembly at block 1012 can include (i) positioning the shape retaining element between a first sheet of foam and a second sheet of foam at block 1020, (ii) after positioning the shape retaining element between the first sheet of foam and the second sheet of foam at block 1020, coupling the first sheet of foam to the second sheet of foam on opposing sides of the shape retaining element at block 1022, and (iii) after coupling the first sheet of foam to the second sheet of foam at block 1022, cutting the first sheet of foam and the second sheet of foam on the opposing sides of the shape retaining element to form the foam sleeve with the shape retaining element positioned in the bore of the foam sleeve at block 1024.

Figure 13:
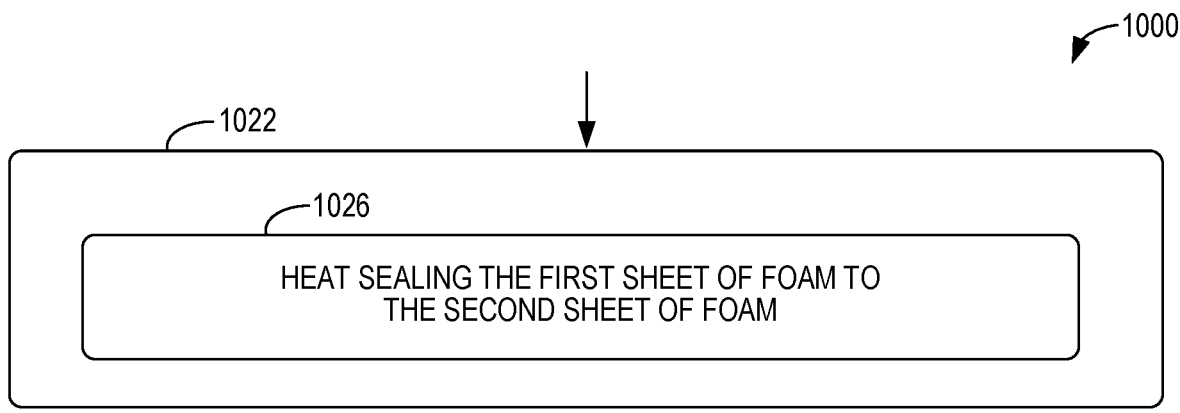
FIG. 13 depicts a flowchart for a process for making a urine collection device for use with the process shown in FIG. 10.

As shown in FIG. 13, coupling the first sheet of foam to the second sheet of foam at block 1022 can include heat sealing the first sheet of foam to the second sheet of foam at block 1026.

Figure 14:
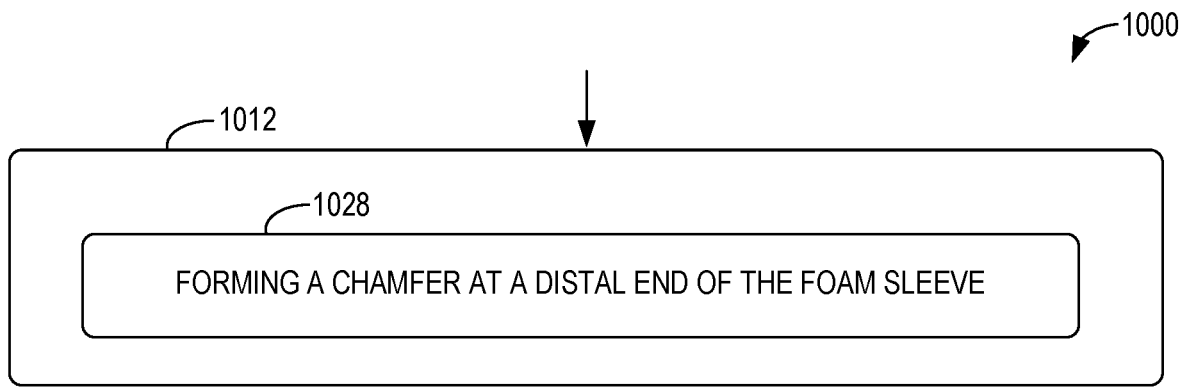
FIG. 14 depicts a flowchart for a process for making a urine collection device for use with the process shown in FIG. 10.

As shown in FIG. 14, forming the fluid collection assembly at block 1012 can include forming a chamfer at a distal end of the foam sleeve at block 1028.

Figure 15:
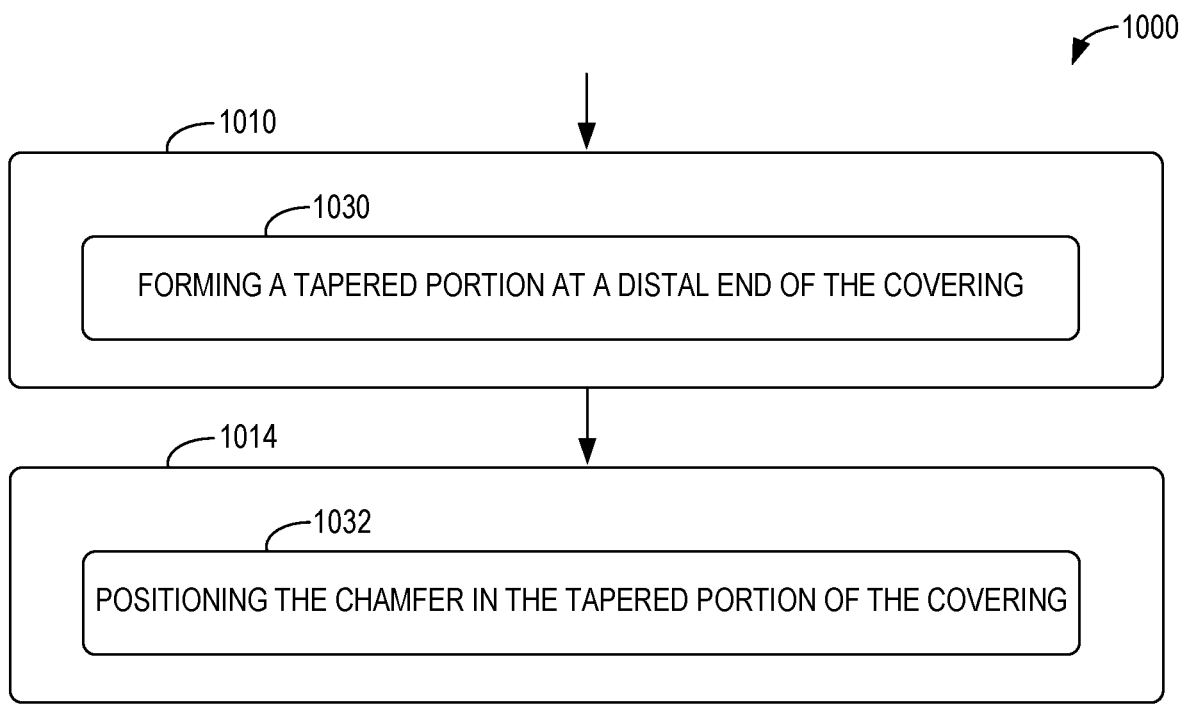
FIG. 15 depicts a flowchart for a process for making a urine collection device for use with the process shown in FIG. 10.

As shown in FIG. 15, forming the covering at block 1010 can include forming a tapered portion at a distal end of the covering at block 1030. Also, in FIG. 15, positioning the fluid collection assembly in the recessed receptacle defined by the covering at block 1014 can include positioning the chamfer in the tapered portion of the covering at block 1032.

Figure 16:
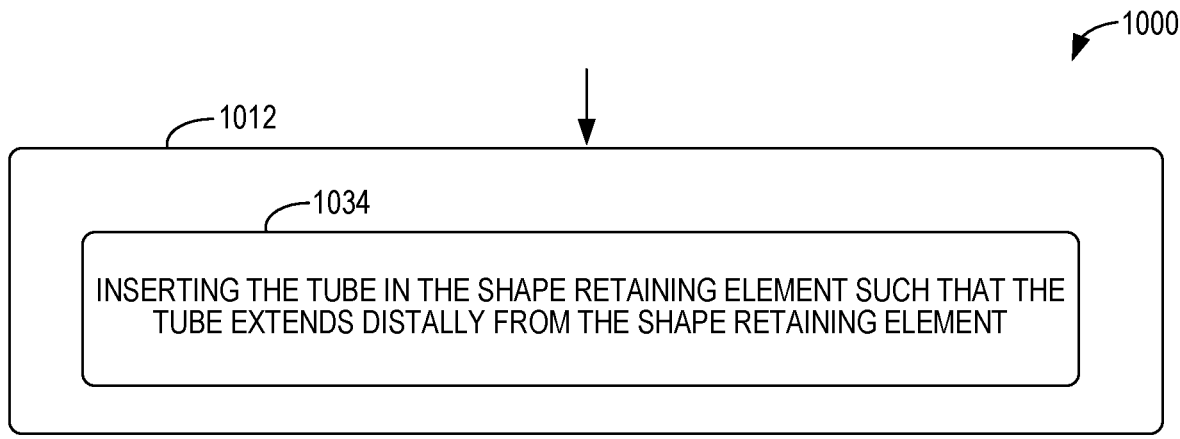
FIG. 16 depicts a flowchart for a process for making a urine collection device for use with the process shown in FIG. 10.

As shown in FIG. 16, forming the fluid collection assembly at block 1012 can include inserting the tube in the shape retaining element such that the tube extends distally from the shape retaining element at block 1034.

Figure 17:
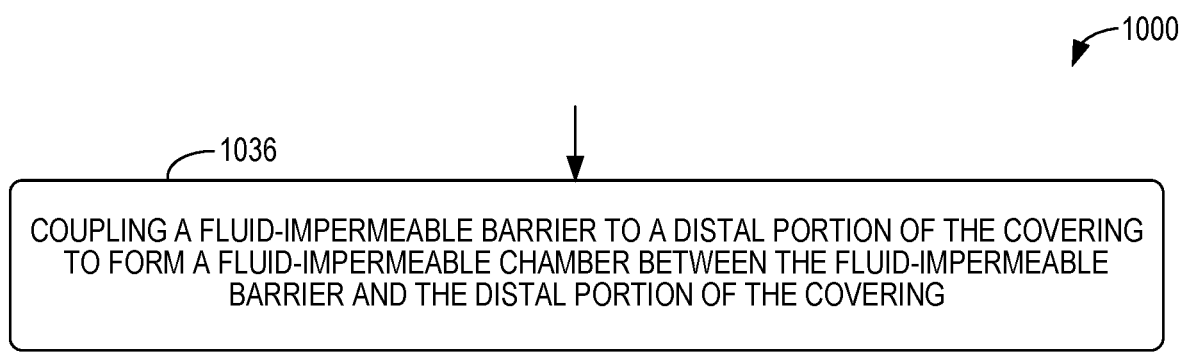
FIG. 17 depicts a flowchart for a process for making a urine collection device for use with the process shown in FIG. 10.

As shown in FIG. 17, the process 1000 can further include coupling a fluid-impermeable barrier to a distal portion of the covering to form a fluid-impermeable chamber between the fluid-impermeable barrier and the distal portion of the covering at block 1036.

Figure 18:
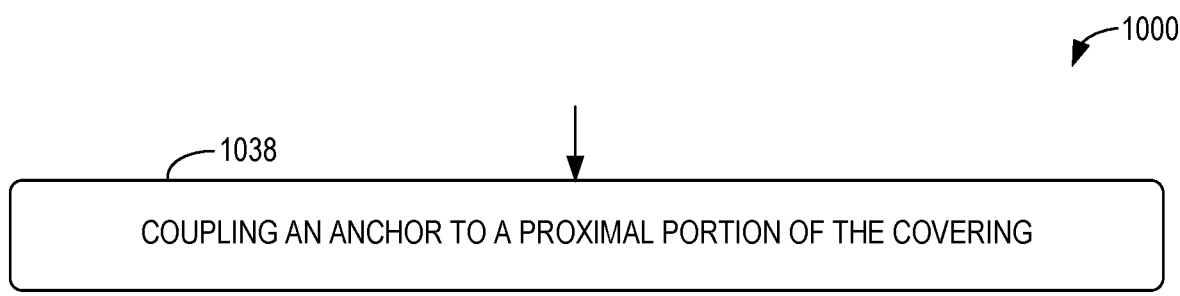
FIG. 18 depicts a flowchart for a process for making a urine collection device for use with the process shown in FIG. 10.

As shown in FIG. 18, the process 1000 can also include coupling an anchor to a proximal portion of the covering at block 1038. The anchor can include an adhesive configured to couple the urine collection device to a patient.

Figure 19:
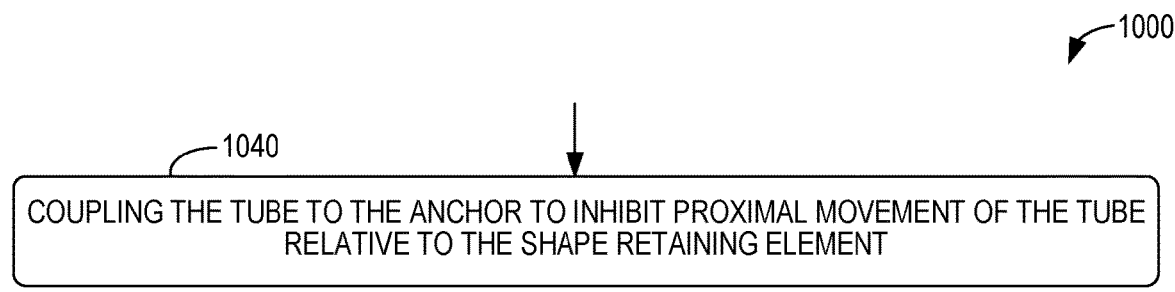
FIG. 19 depicts a flowchart for a process for making a urine collection device for use with the process shown in FIG. 10.

As shown in FIG. 19, the process 1000 can also include coupling the tube to the anchor to inhibit proximal movement of the tube relative to the shape retaining element at block 1040.

Figure 20:
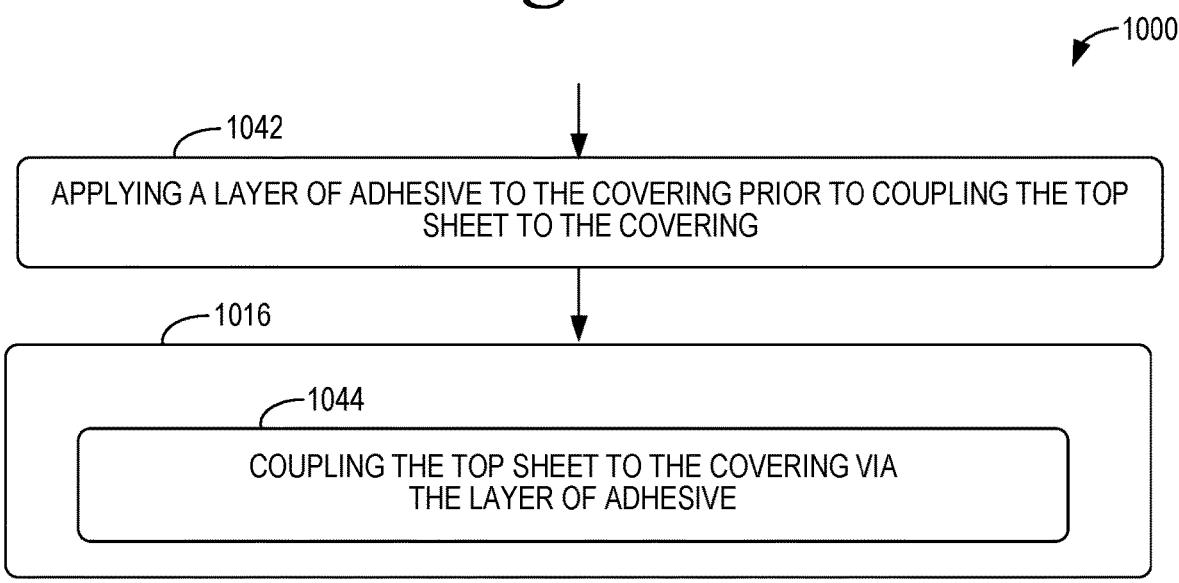
FIG. 20 depicts a flowchart for a process for making a urine collection device for use with the process shown in FIG. 10.

As shown in FIG. 20, the process 1000 can further include applying a layer of adhesive to the covering at block 1042 prior to coupling the top sheet to the covering at block 1016.

Additionally, in FIG. 20, coupling the top sheet to the covering at block 1016 can include coupling the top sheet to the covering via the layer of adhesive at block 1044.

Figure 21:
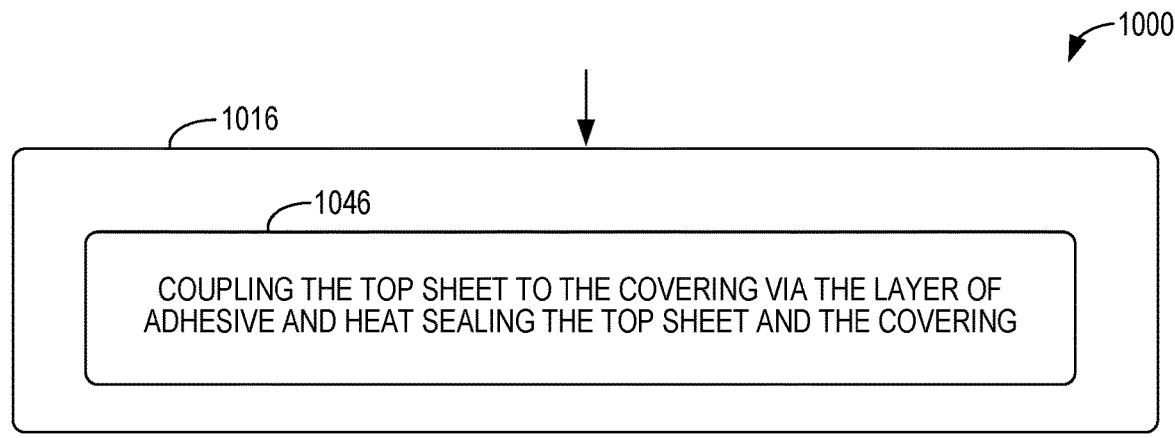
FIG. 21 depicts a flowchart for a process for making a urine collection device for use with the process shown in FIG. 10.

As shown in FIG. 21, coupling the top sheet to the covering at block 1016 can include coupling the top sheet to the covering via the layer of adhesive and heat sealing the top sheet and the covering at block 1046.

Figure 22:
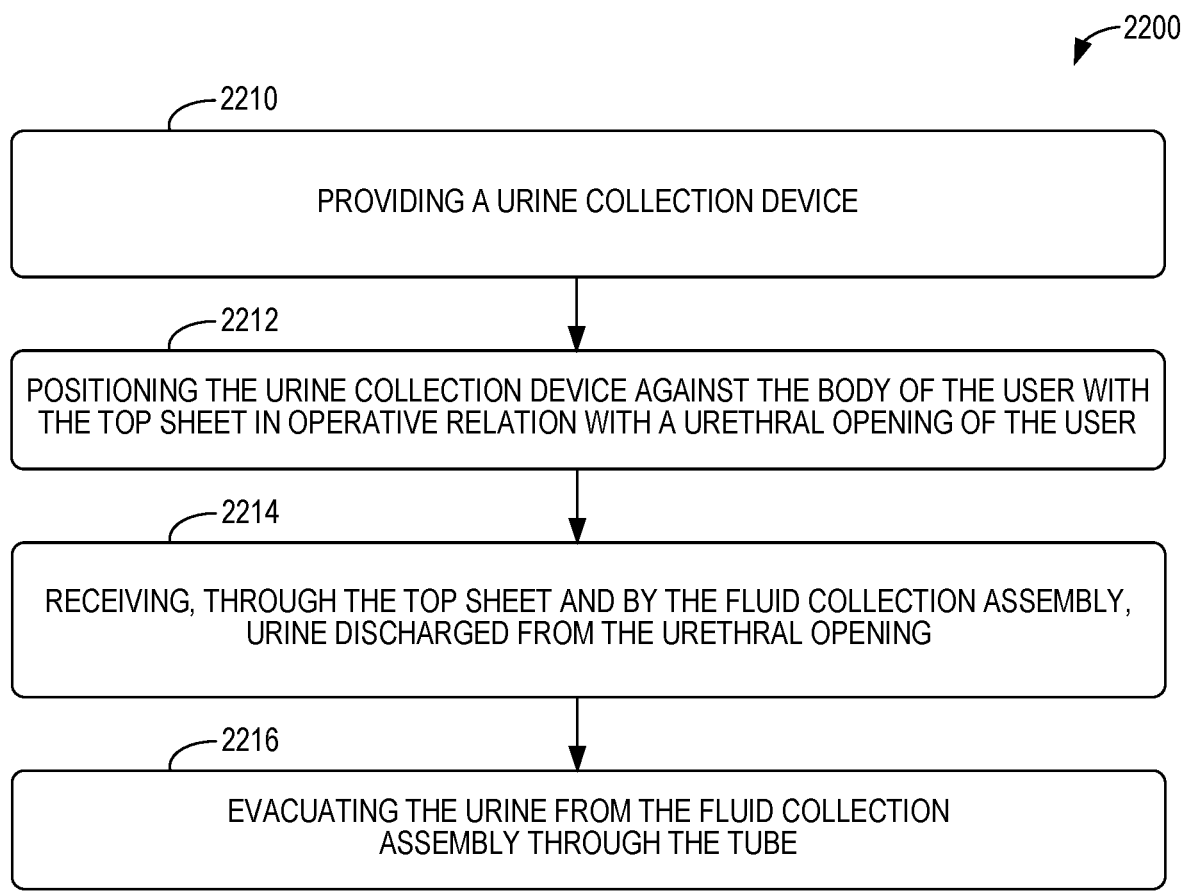
FIG. 22 depicts a simplified block diagram of a system for making a urine collection device, according to an example.

Referring now to FIG. 22, a flowchart for a process 2200 of collecting urine discharged from a body of a user is shown according to an example. As shown in FIG. 22, at block 2210, the process 2200 includes providing a urine collection device. The urine collection device includes a covering defining a recessed receptacle, and a fluid collection assembly positioned in the recessed receptacle defined by the covering. The fluid collection assembly includes (i) a foam sleeve including a bore extending from a first end of the foam sleeve to a second end of the foam sleeve and (ii) a shape retaining element positioned in the bore of the foam sleeve. The shape retaining element is configured to conform the fluid collection assembly to a curved configuration for placement against a body of a user and maintain the curved configuration of the fluid collection assembly until the curved configuration is adjusted. The shape retaining element defines a passage extending from between a proximal end of the shape retaining element and a distal end of the shape retaining element. The fluid collection assembly also includes (iii) a tube extending through the passage defined by the shape retaining element. The urine collection further includes a top sheet coupled to the covering. The top sheet and the covering define an internal chamber of the urine collection device. The top sheet is configured to draw urine into the internal chamber and toward the fluid collection assembly.

At block 2212, the process 2200 includes positioning the urine collection device against the body of the user with the top sheet in operative relation with a urethral opening of the user. At block 2214, the process 2200 includes receiving, through the top sheet and by the fluid collection assembly, urine discharged from the urethral opening. At block 2216, the process 2200 includes evacuating the urine from the fluid collection assembly through the tube.

Figure 23:
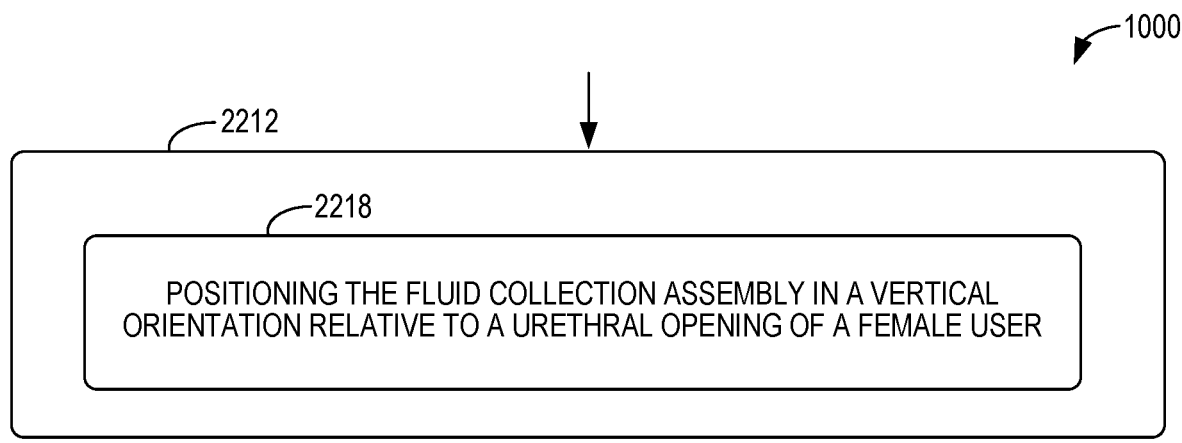
FIG. 23 depicts a flowchart for a process for collecting urine discharged from a body of a user for use with the process shown in FIG. 22.
Figure 24:
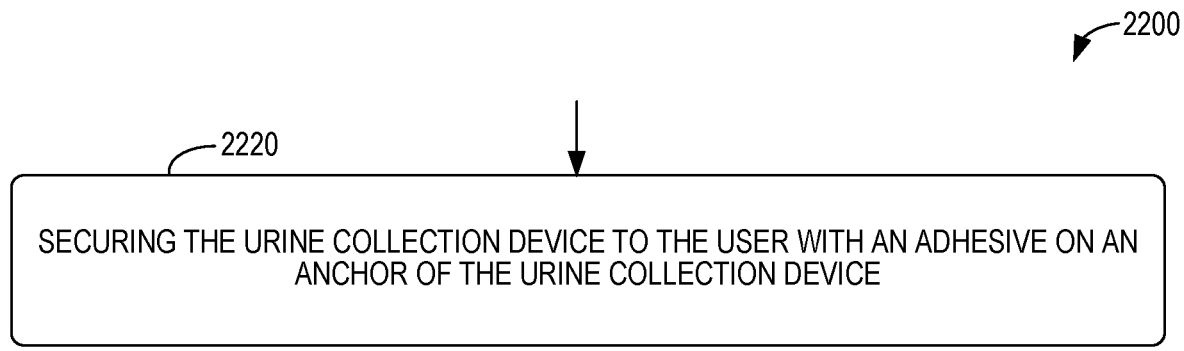
FIG. 24 depicts a flowchart for a process for collecting urine discharged from a body of a user for use with the process shown in FIG. 22.
Figure 25:
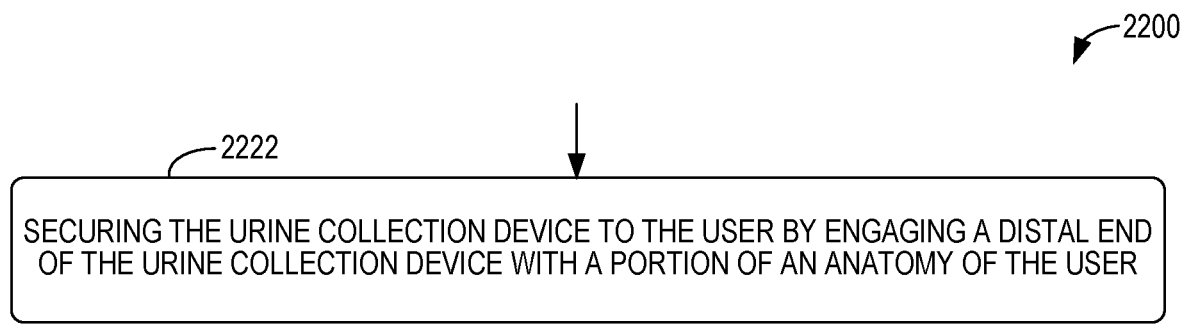
FIG. 25 depicts a flowchart for a process for collecting urine discharged from a body of a user for use with the process shown in FIG. 22.

FIGS. 23-25 depict additional aspects of the process 2200 according to further examples. As shown in FIG. 23, positioning the urine collection device against the body of the user at block 2212 can include positioning the fluid collection assembly in a vertical orientation relative to a urethral opening of a female user at block 2218.

As shown in FIG. 24, the process 2200 can also include securing the urine collection device to the user with an adhesive on an anchor of the urine collection device at block 2220.

As shown in FIG. 25, the process 2200 can further include securing the urine collection device to the user by engaging a distal end of the urine collection device with a portion of the user's anatomy at block 2222.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A urine collection device, comprising:
a covering defining a recessed receptacle, wherein the covering comprises an upper peripheral edge;
a fluid collection assembly positioned in the recessed receptacle defined by the covering, wherein the fluid collection assembly comprises:
a foam sleeve comprising a bore extending from a first end of the foam sleeve to a second end of the foam sleeve,
a shape retaining element positioned in the bore of the foam sleeve, wherein the shape retaining element is configured to conform the fluid collection assembly to a curved configuration for placement against a body of a user and maintain the curved configuration of the fluid collection assembly until the curved configuration is adjusted, wherein the shape retaining element defines a passage extending between a distal end of the shape retaining element and a proximal end of the shape retaining element,
a tube extending through the passage defined by the shape retaining element; and
a top sheet coupled to the upper peripheral edge of the covering,
wherein the top sheet and the covering define an internal chamber of the urine collection device,
wherein a distal end of the covering defines a distal end of the internal chamber,
wherein the top sheet extends above and across the recessed receptacle of the covering such that the top sheet defines a top of the internal chamber, and
wherein the top sheet is configured to draw urine into the internal chamber and toward the fluid collection assembly.

2. The urine collection device of claim 1, wherein the upper peripheral edge of the covering tapers inwardly toward a center axis of the covering such that the covering comprises a tapered portion at a distal end of the covering.

3. The urine collection device of claim 2, wherein the foam sleeve extends into the tapered portion at the distal end of the covering.

4. The urine collection device of claim 3, wherein the foam sleeve comprises a chamfer at the tapered portion of the covering.

5. The urine collection device of claim 2, wherein the tube extends distally from the shape retaining element into the tapered portion at the distal end of the covering.

6. The urine collection device of claim 5, wherein a distal end of the tube is approximately flush with the first end of the foam sleeve.

7. The urine collection device of claim 1, wherein the tube comprises a plurality of apertures at a distal portion of the tube.

8. The urine collection device of claim 1, further comprising a fluid-impermeable barrier coupled to a distal portion of the covering, wherein the fluid-impermeable barrier and the distal portion of the covering define a fluid-impermeable chamber.

9. The urine collection device of claim 1, wherein the top sheet comprises a fibrous material that is configured to draw the urine toward the fluid collection assembly under capillary action.

10. The urine collection device of claim 1, further comprising an anchor coupled to a proximal portion of the covering, wherein the anchor comprises an adhesive configured to couple the urine collection device to the user. a foam.

11. The urine collection device of claim 1, wherein the covering comprises a foam.

12. The urine collection device of claim 1, further comprising one or more vent apertures extending through the covering.

13. A method of making a urine collection device, comprising:
forming a covering such that the covering defines a recessed receptacle;
forming a fluid collection assembly comprising:
a foam sleeve comprising a bore extending from a first end of the foam sleeve to a second end of the foam sleeve,
a shape retaining element positioned in the bore of the foam sleeve, wherein the shape retaining element is configured to conform the fluid collection assembly to a curved configuration for placement against a body of a user and maintain the curved configuration of the fluid collection assembly until the curved configuration is adjusted, wherein the shape retaining element defines a passage extending from between a distal end of the shape retaining element and a proximal end of the shape retaining element, and
a tube extending through the passage defined by the shape retaining element;
after forming the covering such that the covering defines the recessed receptacle, positioning the fluid collection assembly in the recessed receptacle defined by the covering; and
after positioning the fluid collection assembly in the recessed receptacle defined by the covering, coupling a top sheet to the covering with the fluid collection assembly positioned between the top sheet and the covering,
wherein the top sheet and the covering define an internal chamber of the urine collection device, and
wherein the top sheet is configured to draw urine into the internal chamber and toward the fluid collection assembly.

14. The method of claim 13, wherein forming the fluid collection assembly comprises:
positioning the shape retaining element between a first sheet of foam and a second sheet of foam;
after positioning the shape retaining element between the first sheet of foam and the second sheet of foam, coupling the first sheet of foam to the second sheet of foam on opposing sides of the shape retaining element; and
after coupling the first sheet of foam to the second sheet of foam, cutting the first sheet of foam and the second sheet of foam on the opposing sides of the shape retaining element to form the foam sleeve with the shape retaining element positioned in the bore of the foam sleeve.

15. The method of claim 14, wherein forming the fluid collection assembly comprises forming a chamfer at a distal end of the foam sleeve.

16. The method of claim 13, further comprising coupling a fluid-impermeable barrier to a distal portion of the covering to form a fluid-impermeable chamber between the fluid-impermeable barrier and the distal portion of the covering, wherein coupling the fluid-impermeable barrier to the distal portion of the covering is performed simultaneously with coupling the top sheet to the covering.

17. The method of claim 13, further comprising applying a layer of adhesive to the covering prior to coupling the top sheet to the covering,
wherein coupling the top sheet to the covering comprises coupling the top sheet to the covering via the layer of adhesive.

18. A method for collecting urine discharged from a body of a user, comprising:
providing a urine collection device, comprising:
a covering defining a recessed receptacle, wherein the covering comprises an upper peripheral edge;
a fluid collection assembly positioned in the recessed receptacle defined by the covering, wherein the fluid collection assembly comprises:
a foam sleeve comprising a bore extending from a first end of the foam sleeve to a second end of the foam sleeve,
a shape retaining element positioned in the bore of the foam sleeve, wherein the shape retaining element is configured to conform the fluid collection assembly to a curved configuration for placement against a body of a user and maintain the curved configuration of the fluid collection assembly until the curved configuration is adjusted, wherein the shape retaining element defines a passage extending from between a distal end of the shape retaining element and a proximal end of the shape retaining element,
a tube extending through the passage defined by the shape retaining element; and
a top sheet coupled to the upper peripheral edge of the covering,
wherein the top sheet and the covering define an internal chamber of the urine collection device,
wherein a distal end of the covering defines a distal end of the internal chamber,
wherein the top sheet extends above and across the recessed receptacle of the covering such that the top sheet defines a top of the internal chamber, and
wherein the top sheet is configured to draw urine into the internal chamber and toward the fluid collection assembly;
positioning the urine collection device against the body of the user with the top sheet in operative relation with a urethral opening of the user;
receiving, through the top sheet and by the fluid collection assembly, urine discharged from the urethral opening; and
evacuating the urine from the fluid collection assembly through the tube.

19. The method according to claim 18, further comprising:
securing the urine collection device to the user with an adhesive on an anchor of the urine collection device; and
securing the urine collection device to the user by engaging a distal end of the urine collection device with a portion of an anatomy of the user,
wherein positioning the urine collection device against the body of the user comprises positioning the fluid collection assembly in a vertical orientation relative to a urethral opening of a female user.

20. The method of claim 13, wherein forming the covering such that the covering defines the recessed receptacle comprises applying thermal energy to a sheet of foam while pressing the sheet of foam into a mold.

* * * * *